US010493032B2

(12) United States Patent
Brunel et al.

(10) Patent No.: US 10,493,032 B2
(45) Date of Patent: *Dec. 3, 2019

(54) NUTRITIONAL AND MEDICINAL ORAL COMPOSITION FOR VETERINARY USE

(71) Applicant: VIRBAC, Carros (FR)

(72) Inventors: Nicolas Brunel, Vallauris (FR); Fanny Martins, Cagnes sur Mer (FR); Patricia Goisnard, Nice (FR)

(73) Assignee: VIRBAC, Carros (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,023

(22) Filed: Nov. 19, 2018

(65) Prior Publication Data

US 2019/0083401 A1  Mar. 21, 2019

Related U.S. Application Data

(63) Continuation of application No. 14/773,141, filed as application No. PCT/IB2014/059403 on Mar. 3, 2014, now Pat. No. 10,166,186.

(30) Foreign Application Priority Data

Mar. 4, 2013 (FR) .................................... 13 51905

(51) Int. Cl.

| | |
|---|---|
| *A61K 9/16* | (2006.01) |
| *A23K 40/25* | (2016.01) |
| *A61K 31/55* | (2006.01) |
| *A23K 40/20* | (2016.01) |
| *A23K 40/30* | (2016.01) |
| *A23K 20/00* | (2016.01) |
| *A23K 20/111* | (2016.01) |
| *A23K 20/158* | (2016.01) |
| *A23K 50/40* | (2016.01) |
| *A61K 9/00* | (2006.01) |

(52) U.S. Cl.

CPC ............ *A61K 9/1676* (2013.01); *A23K 20/00* (2016.05); *A23K 20/111* (2016.05); *A23K 20/158* (2016.05); *A23K 40/20* (2016.05); *A23K 40/25* (2016.05); *A23K 40/30* (2016.05); *A23K 50/40* (2016.05); *A61K 9/0053* (2013.01); *A61K 9/1694* (2013.01); *A61K 31/55* (2013.01)

(58) Field of Classification Search

CPC .... A61K 9/1676; A61K 31/55; A61K 9/0053; A61K 9/1694; A23K 40/20; A23K 40/25; A23K 20/00; A23K 20/111; A23K 20/158; A23K 50/40; A23K 40/30

See application file for complete search history.

(56) References Cited

U.S. PATENT DOCUMENTS

| | | | |
|---|---|---|---|
| 2002/0142050 A1 | 10/2002 | Straub et al. | |
| 2004/0197352 A1 | 10/2004 | Ranganathan | |
| 2006/0228448 A1 | 10/2006 | Boileau et al. | |
| 2010/0196466 A1* | 8/2010 | Cherukuri | A23G 3/54 424/452 |
| 2010/0233756 A1* | 9/2010 | Sunvold | A23K 40/20 435/34 |
| 2010/0303968 A1 | 12/2010 | Sunvold et al. | |
| 2011/0027418 A1 | 2/2011 | Horgan et al. | |
| 2011/0263560 A1* | 10/2011 | Breitenstein | C07D 211/60 514/210.18 |
| 2016/0008373 A1 | 1/2016 | Brunel et al. | |

FOREIGN PATENT DOCUMENTS

| | | | |
|---|---|---|---|
| EP | 1247456 A2 | | 10/2002 |
| GB | 2003481 A | * | 3/1979 |
| GB | 2209937 A | | 6/1989 |
| WO | 96/22028 A1 | | 7/1996 |
| WO | 01/35925 A1 | | 5/2001 |
| WO | 01/49272 A2 | | 7/2001 |
| WO | 03/075895 A1 | | 9/2003 |
| WO | 2007/084986 A2 | | 7/2007 |
| WO | WO 2007084986 A2 | * | 7/2007 |
| WO | 2010/030614 A2 | | 3/2010 |
| WO | 2010/138372 A2 | | 12/2010 |
| WO | 2011/060945 A2 | | 5/2011 |
| WO | 2011/091111 A1 | | 7/2011 |
| WO | 2012/099786 A1 | | 7/2012 |

OTHER PUBLICATIONS

MSDS for Benazepril, Sep. 12, 2012.*
Apr. 29, 2014 International Search Report issued in International Patent Application No. PCT/IB2014/059403.
Apr. 29, 2014 Written Opinion issued in International Patent Application No. PCT/IB2014/059403.
Apr. 29, 2014 Search Report issued in International Patent Application No. PCT/IB2014/059404.

(Continued)

*Primary Examiner* — Blessing M Fubara
(74) *Attorney, Agent, or Firm* — Oliff PLC

(57) ABSTRACT

The invention relates to a nutritional and medicinal oral composition for veterinary use, including a core of complete feed extrudate coated with at least one layer of fat. The layer of fat includes at least one medicinal agent which includes: (i) at least one preconditioned active principle in the form of a solution or a suspension of said active principle in an oily liquid, or (ii) at least one preconditioned active principle in the form of waxy granules.

6 Claims, 4 Drawing Sheets

(56) References Cited

OTHER PUBLICATIONS

Apr. 29, 2014 Written Opinion issued in International Patent Application No. PCT/IB2014/059404.
Oct. 26, 2017 Office Action issued in U.S. Appl. No. 14/773,168.
Mar. 17, 2017 Office Action issued in U.S. Appl. No. 14/773,141.
Oct. 31, 2016 Office Action issued in U.S. Appl. No. 14/773,141.
Mayo Clinic, "Diseases and Conditions", Cancer Prevention, pp. 1-13, 2015.
May 8, 2017 Office Action issued in U.S Appl. No. 14/773,168.
Jul. 19, 2017 Office Action issued in U.S. Appl. No. 14/773,168.
Oct. 6, 2017 Office Action issued in U.S. Appl. No. 14/773,141.
Hsieh et al. JP 2012149026, 2012. Title and Eng Abstract.
Feb. 12, 2018 Office Action issued in U.S. Appl. No. 14/773,168.
Apr. 13, 2018 Office Action issued in U.S. Appl. No. 14/773,141.
Sep. 21, 2018 Office Action issued in U.S. Appl. No. 14/773,168.
Aug. 14, 2018 Notice of Allowance issued in U.S. Appl. No. 14/773,141.
Aug. 31, 2018 Notice of Allowability issued in U.S. Appl. No. 14/773,141.

\* cited by examiner

NUTRITIONAL AND MEDICINAL ORAL COMPOSITION FOR VETERINARY USE

This is a Continuation of application Ser. No. 14/773,141 filed Sep. 4, 2015, which in turn is now allowed and is a national stage entry of PCT/IB2014/059403 filed Mar. 3, 2014, which claims priority to French Patent Application No. 13 51905 filed Mar. 4, 2013. The disclosure of each of the prior applications is hereby incorporated by reference herein in its entirety.

FIELD OF THE INVENTION

The present invention relates to the field of oral compositions for veterinary use intended for preventing or treating disorders or pathologies in mammals, especially companion animals.

PRIOR ART

The methods for breeding farm animals and the practices for maintaining the well-being of companion animals may require the administration of active pharmaceutical ingredients to these animals.

In both of these contexts relating to the maintenance of animal health, it is important that the active pharmaceutical ingredients are administered in appropriate quality and quantity.

For farm animals, which include pigs, sheep, cattle, goats and poultry, medicinal products, notably antibiotic active principles, are generally mixed extemporaneously in the feed or in water. In fact, feed for farm animals that is ready to use and comprises medicinal products in its composition is considered to represent a very small proportion of feed that is marketed. It may be added that this medicated feed should be offered for a variety of active principles or combinations of active principles, and for a variety of combinations of nutrient elements adapted to each species of farm animals. As a result, the costs of manufacture of medicated feed for farm animals would not be compatible with the economic constraints of the agro-food industry. In general, medicinal products intended for farm animals are in the form of granules, which are mixed extemporaneously with the feed, for example with fodder or with cereal-based pellets. However, these practices do not allow precise control of the amount of medicinal product actually ingested by the animals, notably because the distribution of the medicated granules in the mass of fodder or in the mass of feed pellets is not homogeneous. As an illustration, the respective individual densities of the feed pellets and medicated granules lead to "demixing", i.e. heterogeneous distribution of the medicated granules in the mass of feed pellets, notably because of decanting of the medicated granules in the mixture of granules. Medicinal products may also be incorporated in the drinking water, provided they are water-soluble and stable in dissolved form.

For companion animals, in particular for dogs and cats, for which the active pharmaceutical ingredients are administered individually rather than collectively, practical experience shows that there are often difficulties connected with poor compliance with the treatments, especially treatments by the oral route. It is known in particular that medicinal products presented separately in solid form, for example in the form of pastilles, pills, soft capsules, hard capsules, and tablets, are not readily accepted by companion animals, especially dogs and cats, even when these solid forms are mixed with their food, and regardless of the form of the food, for example mash or pellets. Poor compliance with medicinal treatments for companion animals is further increased when the active principle has a pronounced taste, for example a bitter taste, owing to the highly developed sense of smell and taste of these animals.

Incorporation of a medicinal product in animal feed means that the characteristics of the final nutritional and medicinal composition must meet the requirements of the regulations governing the marketing of health products. A marketing authorization will only be granted if, notably, it is established with certainty that the target dose of active principle is administered to the animal accurately and reproducibly. The method for preparing the composition must therefore be perfectly controlled.

Various solutions have been proposed for supplying medicinal products for oral administration that are able to ensure good compliance of the animals with treatment.

Specifically for farm animals, feed pellets coated with a cohesive gel containing the active principle have been proposed (see PCT application No. WO 96/22028).

For companion animals, a variety of solutions has also been proposed, in particular for reducing the problems of compliance with preventive or therapeutic medicinal treatments, quite particularly the problems of compliance with medicinal treatments for dogs and cats.

For example, European patent application No. EP 1 247 456 describes pharmaceutical compositions in the form of tablets in which the active principle is mixed with an appetizing agent comprising one or more natural or artificial flavors, notably brewer's yeast, the appetizing agent being intended notably to mask the taste of the active principle. A solution based on a similar principle is disclosed in PCT application No. WO 03/075895, which describes tablets, notably based on brewer's yeast, in the mass of which composite particles are dispersed comprising the active principle of interest. The composite particles are formed from a core of inert support that is coated with a layer containing the active principle, the layer of active principle itself being covered with an outer protective layer of a polymer material intended to mask the taste of the active principle. In the tablets described in this document, the particles of active principle are present in the tablet mass, for example the mass consisting of brewer's yeast, which has the function of an appetizing agent. Moreover, the technique employed in this document requires the availability of complex and expensive equipment.

In order to overcome the problems of compliance with therapeutic treatments in animals, PCT application No. WO 01/49272 proposes solid oral formulations of veterinary medicinal products comprising, within a molded mass containing lipids and aromatic agents, granules containing the active principle. In these granules, the active principle is micro-encapsulated in a polymer matrix, in particular an ethylcellulose matrix.

Food supplements in which the active principle of interest is incorporated have also been described.

We may mention PCT application No. WO 01/35925, which describes veterinary food products comprising an active pharmaceutical ingredient, and in which the taste of said active principle is masked, said active principle also being protected against degradation. This document describes in particular microparticles consisting of calcium alginate gel, in the mass of which an active principle of interest is incorporated, said microparticles themselves being enclosed in a material containing powdered biscuit and flour, the mixture being made cohesive owing to the presence of a binder.

In general, the methods of manufacture of pellets for animals comprise a step of obtaining a crude extrudate core comprising a mixture of nutrients (e.g. proteins, lipids, carbohydrates), and in a final step of the method, this core of extrudate is coated hot with a layer of fat or oil, generally by vapor deposition or spraying of the liquefied fat or heated oil on the surface of the crude extrudate core. After cooling, the end product is obtained, which is an extrudate treated by application of fat or oil (also called "treated extrudate"). In the final step of the method, the main functions of heating of the fat or oil are (i) liquefying the fat or oil in order to allow coating of the crude extrudate by vapor deposition or spraying and (ii) if necessary, sterilizing the surface of the crude extrudate by heat and protecting the surface of the crude extrudate against colonization by pathogenic microorganisms, such as pathogenic bacteria of the genus *Salmonella*.

The preparation of pellets for animals, where the core is coated with a layer of animal or vegetable fat according to the general method described above, is notably illustrated in PCT application No. WO 2012/099786. According to this method, the fat composition is first liquefied by heating, for example to a temperature of about 125° C., then the liquid fat is sprayed onto the core of the pellets, and then the pellets thus treated are conveyed to a vibrating air-fluidized bed cooling device. Other methods of obtaining pellets for animals comprising a step of hot application of an outer coating layer of fat or oil are described notably in patent application No. US 2010/0303968 and in PCT applications Nos. WO 2010/138372 and WO 2011/091111. Moreover, a great many of the known methods comprise a final step of drying the pellets at high temperature, for example at a temperature of 140° C., as described for example in the aforementioned PCT application No. WO 2011/091111.

The type of method described above, comprising a final step of high-temperature coating of a crude extrudate with a fat or a liquefied oil, has also been used in the prior art for making pellets for animals comprising, within the coating of the final coated extrudate with fat, one or more additives, called "active" additives, which may be beneficial for the nutrition or health of the animal.

An illustration of such a method for obtaining pellets comprising an active pharmaceutical ingredient is presented in PCT application No. WO 2010/030614. This document describes the manufacture of pellets for animals possessing a protein core ("crude extrudate"), in which the protein core is coated with an additional layer that may contain one or more so-called "active" additives or components, such as sugars, gums, animal or vegetable proteins, vitamins, fatty acids, or biological agents such as probiotic microorganisms and enzymes. This document describes in particular a method of manufacturing pellets comprising a core based on vegetable proteins, which is coated with a layer of fat comprising a probiotic microorganism. The cores based on vegetable proteins are prepared in a first step of the method. Then the core coating composition is prepared by mixing together the probiotic microorganisms and a fat composition. Then the cores are coated with a layer of the mixture of fat and probiotics by placing the cores in an air-type fluidized bed mixer and by supplying the air-type fluidized bed mixer with the mixture of fat and probiotics, which has been liquefied beforehand by heating, for example at a temperature of 56° C. After a cooling step, the end product (also called "treated extrudate") is obtained. All these techniques involve a high-temperature step in the presence of active principles, which causes a varying degree of degradation of the active principle.

There is a need for oral veterinary nutritional and medicinal compositions, alternative or improved relative to the known compositions, that allow stable and effective incorporation of sensitive and/or bitter active principles and that can be manufactured at an acceptable cost for the animal feed industry.

There is also a need for improved methods for preparing oral veterinary nutritional and medicinal compositions.

SUMMARY OF THE INVENTION

The present invention provides a method for obtaining a nutritional and medicinal oral composition for veterinary use comprising the following steps:
  a) supplying cores of feed extrudate, and
  b) coating the cores of complete feed extrudate supplied in step a) with at least one layer of fat comprising at least one medicinal agent, said medicinal agent comprising (i) at least one preconditioned active principle in the form of a solution or a suspension of said active principle in an oily liquid or (ii) at least one preconditioned active principle in the form of waxy granules, at a temperature below 40° C.

In certain embodiments of the method, step b) comprises the following steps:
  b1) bringing the cores of complete feed extrudate supplied in step a) into contact with at least one medicinal agent, said medicinal agent comprising (i) at least one preconditioned active principle in the form of a solution or of a suspension of said active principle in an oily liquid or (ii) at least one preconditioned active principle in the form of waxy granules, and
  b2) coating the extrudate cores obtained at the end of step b1) with at least one layer of fat, at a temperature below 40° C.

In other embodiments of the method, step b) comprises the following steps:
  b3) obtaining a fat composition comprising a medicinal agent, said medicinal agent comprising (i) at least one preconditioned active principle in the form of a solution or of a suspension of said active principle in an oily liquid or (ii) at least one preconditioned active principle in the form of waxy granules, and
  b4) coating the extrudate cores obtained at the end of step a) with at least one layer of the fat composition comprising said active principle obtained at the end of step b3), at a temperature below 40° C.

For the purposes of the present description, the term "active principle" denotes an active pharmaceutical ingredient accepted by a person skilled in the art, i.e. a substance that is included in the composition of a medicinal product and that endows said medicinal product with its preventive or curative therapeutic properties.

For the purposes of the present description, a preconditioned active principle in dissolved form or in suspension in an oily liquid or in the form of waxy granules may also be called "medicinal agent" or "medicated premix".

The coating layer of fat comprises at least one fat of animal or vegetable origin.

In certain embodiments of the method, the layer of fat is solid at a temperature below 25° C. The fat can then be worked by kneading or mixing without adding heat, to obtain a fluid texture suitable for use as a coating agent. The layer of fat may comprise at least one fat selected from hog fat, lard, suet, duck fat or fish oil.

In other embodiments, the layer of fat is liquid at a temperature of 25° C. The layer of fat may for example comprise a fish oil.

In certain embodiments of the method, the active principle(s) included in the medicinal agent is(are) sensitive to moisture.

In certain embodiments of the method, the active principle is intended for preventing or treating a disorder or a chronic disease or a disease requiring long and repeated treatment, for example daily. Such diseases may be hepatic, renal, vascular, digestive, inflammatory, infectious or respiratory-tract chronic diseases, for example renal insufficiency, or cancer. The active principle may thus be selected from metronidazole, neomycin, bronchodilators such as aminophylline, nonsteroidal anti-inflammatories such as carprofen, meloxicam, robenacoxib, mavacoxib, firocoxib, deracoxib, ciclosporin, S-adenosyl-methionine, beta-blockers, aldosterone receptor inhibitors, such as eplerenone or spironolactone, amlodipine, pimobendan, levosimendan, torasemide, furosemide, alkaloids such as theophylline, anti-angiogenic agents etc. In the case of renal insufficiency in particular, said active principle may be selected from angiotensin-converting enzyme inhibitors (ACE inhibitors), inhibitors of renin and antagonists of the angiotensin II receptor (compounds ending in "-sartan" such as losartan).

The angiotensin-converting enzyme inhibitors may be selected from benazepril, enalapril, ramipril, quinapril, preindopril, lisinopril, imidapril, zofnopril, trandolapril, as well as salts thereof.

The invention supplies a nutritional and medicinal oral composition for veterinary use, which may also be called medicated feed, comprising a core of complete feed extrudate, said core being coated with at least one layer of fat, said layer of fat comprising at least one active principle in the form of particles, said active principle being preconditioned in dissolved form or in suspension in an oily liquid or in the form of waxy granules.

The present invention also relates to the use of a composition as defined above, for making a nutraceutical for preventing or treating a chronic disease or one requiring daily treatment, for example renal insufficiency in a nonhuman mammal, in particular dogs and cats.

It also relates to a premix composition for making a nutritional and medicinal composition comprising an oily suspension of particles of non-microencapsulated benazepril.

According to the invention, a medicated premix composition is also supplied, for making a nutritional and medicinal composition comprising particles of non-microencapsulated benazepril distributed in a hydrophobic medium comprising at least one wax, in the form of waxy granules.

DESCRIPTION OF THE FIGURES

FIG. 1 illustrates the theoretical profiles of pharmacological effect of:

FIGS. 1A and 1B show (i) curve of plasma concentration of benazeprilat (plasma metabolite of benazepril) obtained by modeling and materialized by the solid curves, expressed in ng/mL (ordinate on left) and (ii) curve representing the percentage ACE (angiotensin-converting enzyme) inhibition materialized by the dotted curves, expressed in percentage ACE inhibition (ordinate on right).

Abscissa: time after first oral administration, expressed in hours.

Figure 2:
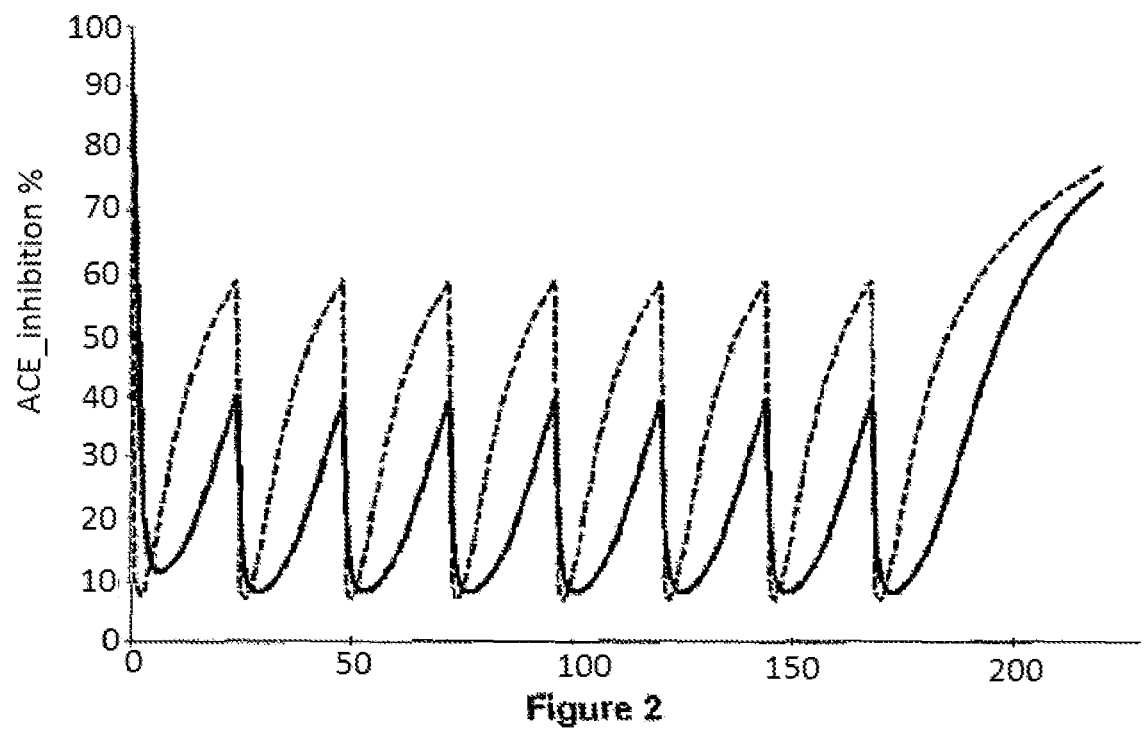

FIG. 2 shows comparison of the theoretical pharmacological effects (i) of the oral veterinary composition described in example 1 (continuous line) and (ii) of the pharmaceutical specialty Fortekor® (discontinuous line) at the same dose of 600 μg/kg of benazeprilat, on plasma ACE inhibition. Ordinate: percentage ACE inhibition. Abscissa: time after first oral administration, expressed in hours.

Figure 3:
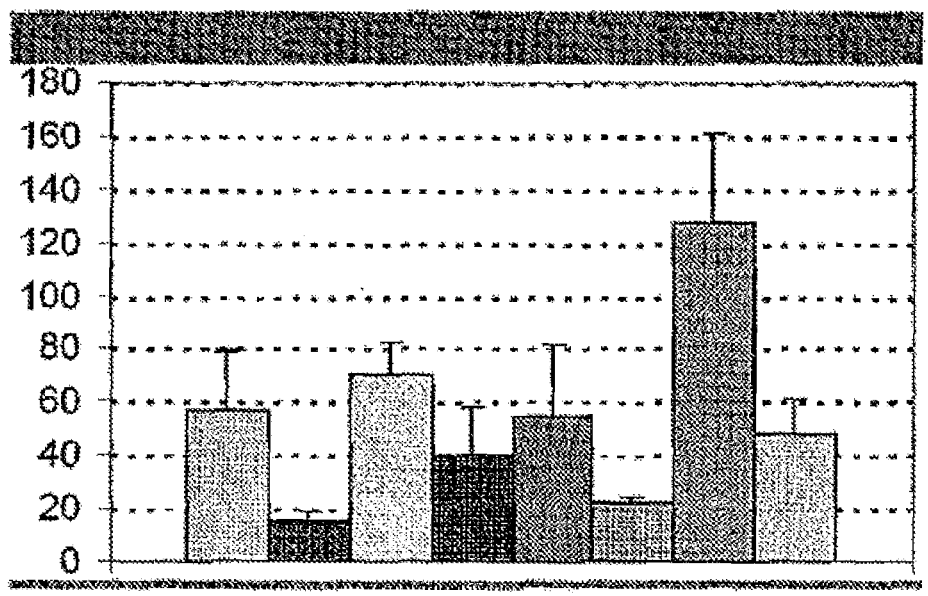

FIG. 3 illustrates the mean (±SD) maximum concentrations (Cmax) of benazeprilat observed on D1 and D8 after treatment with Fortekor (column with squares) versus the composition according to the invention (Inv) (filled column) during studies A and B. Ordinate: plasma concentration of benazeprilat, expressed in g/L. Abscissa, from left to right: (1) Study A, Fortekor Day 1, (2) Study A, Inv Day 1, (3) Study B, Fortekor Day 1, (4) Study B, Inv Day 1, (5) Study A, Fortekor Day 8, (6) Study A, Inv Day 8, (7) Study B, Fortekor Day 8, (8) Study B, Inv Day 8.

Figure 4:
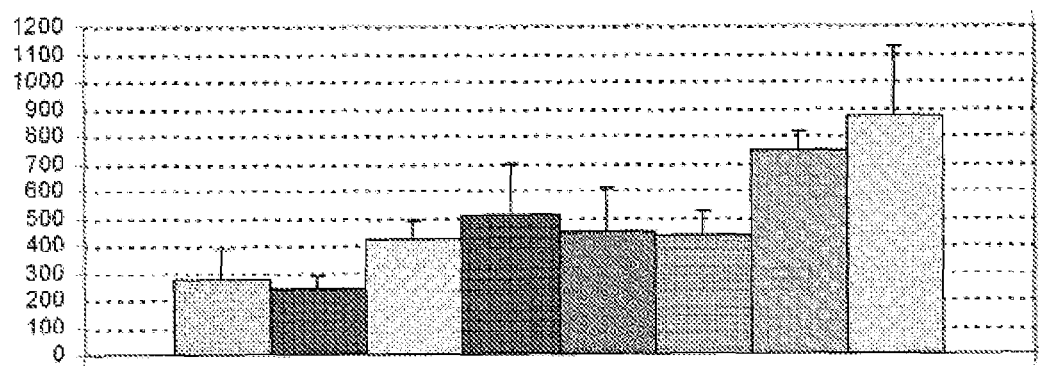

FIG. 4 illustrates the area under the curve of the plasma concentrations of benazeprilat AUC last mean benazeprilat (±SD) on D1 and D8 after treatment with Fortekor versus the composition according to the invention during studies A and B. Ordinate: Mean value of AUC Last, expressed in μg·h/L of benazepril. Abscissa, from left to right: (1) Study A, Fortekor Day 1, (2) Study A, VIRBAC Day 1, (3) Study B, Fortekor Day 1, (4) Study B, Inv Day 1, (5) Study A, Fortekor Day 8, (6) Study A, Inv Day 8, (7) Study B, Fortekor Day 8, (8) Study B, Inv Day 8.

Figure 5:
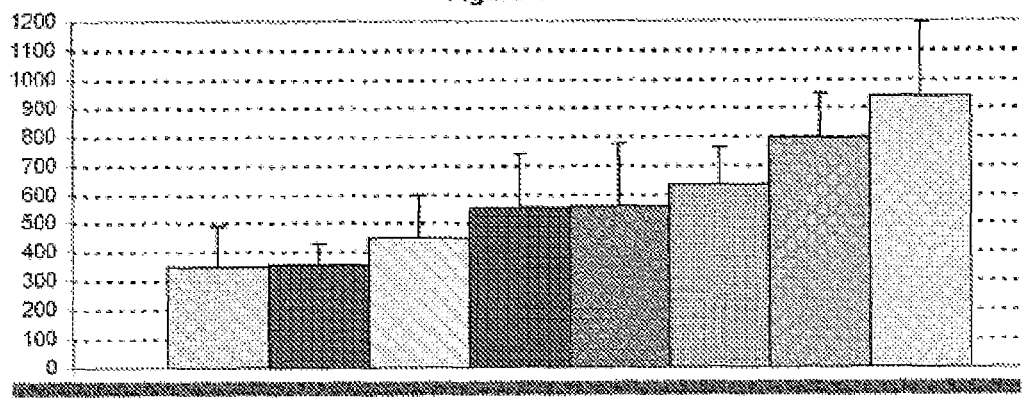

FIG. 5 illustrates the area under the curve of the mean (±SD) plasma concentrations of benazeprilat (AUC last corr) on D1 and D8 after treatment with Fortekor versus the composition according to the invention during studies A and B. Ordinate: Value of AUC Last corr, expressed in μg·h/L of benazepril. Abscissa, from left to right: (1) Study A, Fortekor Day 1, (2) Study A, Inv. Abscissa, from left to right: (1) Study A, Fortekor Day 1, (2) Study A, Inv Day 1, (3) Study B, Fortekor Day 1, (4) Study B, Inv Day 1, (5) Study A, Fortekor Day 8, (6) Study A, Inv Day 8, (7) Study B, Fortekor Day 8, (8) Study B, Inv Day 8.

Figure 6:
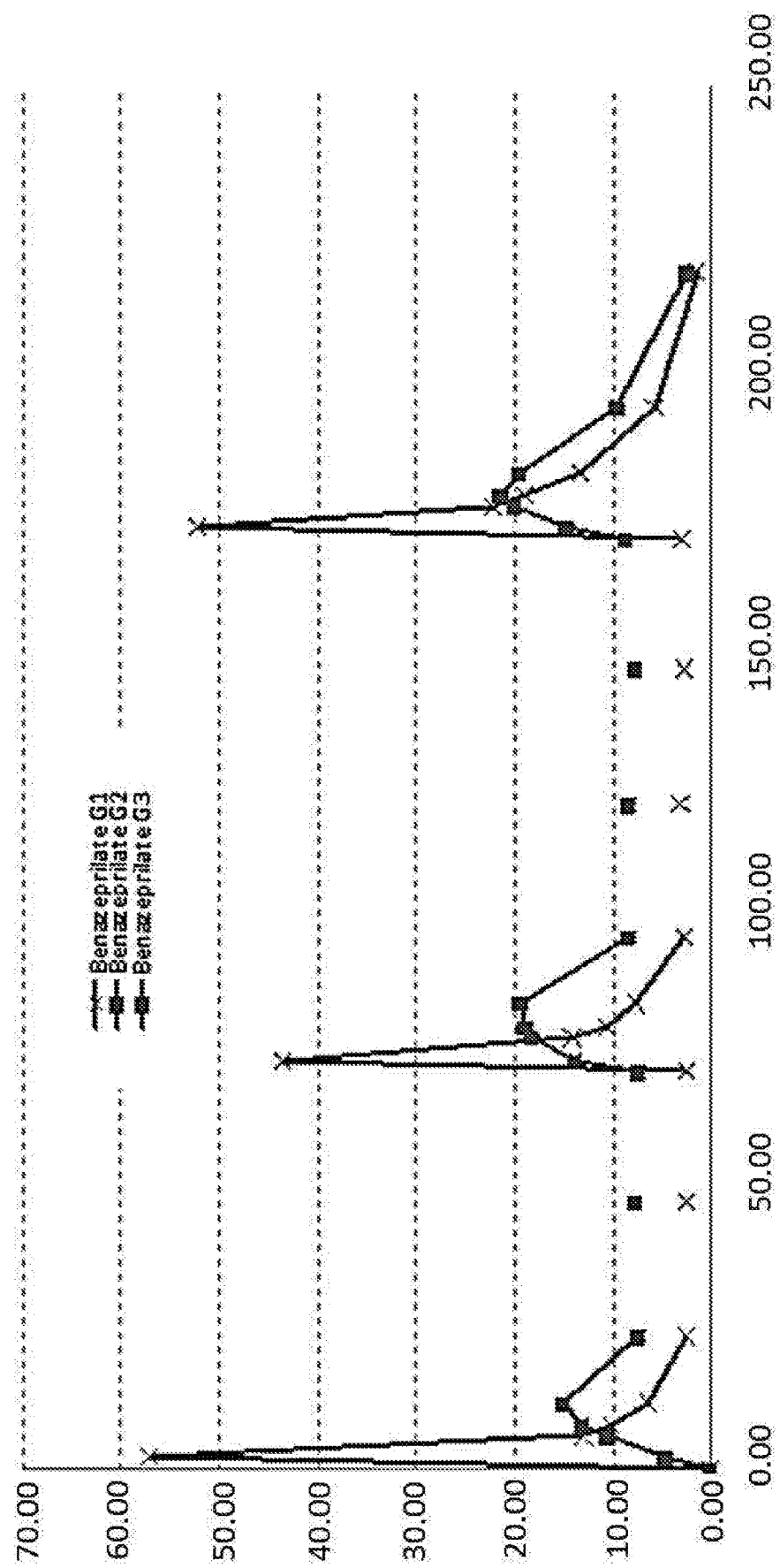

FIG. 6 illustrates a comparison of the pharmacokinetic profiles of benazeprilat after administration of the composition Inv (squares) and of the composition Fortekor (crosses) respectively. Ordinate: plasma concentration of benazeprilat, expressed in ng/ml. Abscissa, comparison of the pharmacokinetic profiles of the composition Fortekor (upper curves with a narrow peak) and of the composition Inv (lower curves with a broad peak), respectively at Time 0, at Time 45 hours and at Time 175 hours. It can be seen that the Cmax of Inv is lower than the Cmax with Fortekor; nevertheless FIGS. 4 and 5 show that the AUCs are comparable, thus giving Inv a better pharmacological profile in toxicological terms, with comparable or even greater efficacy.

DETAILED DESCRIPTION OF THE INVENTION

The present invention provides a method for preparing a nutritional and medicinal oral composition, for veterinary use.

The present invention also provides novel oral veterinary compositions that are both nutritional and medicinal.

The applicant became aware that there was a need for compositions intended for animals that include both (i) the constituents necessary for complete nutrition of these animals and (ii) one or more active principles intended to prevent or treat disorders or pathologies that could affect, or that do affect, said animals.

The applicant therefore undertook to develop compositions for veterinary use for oral administration comprising nutrient elements present in a suitable quality and quantity for complete nutrition of the animals, said compositions also including at least one active principle that is present in suitable quality or quantity for preventing or treating a disorder or a disease in said animals.

To achieve this objective, the applicant undertook to identify solutions that allow the coexistence, within one and the same oral composition, of the substances necessary for constituting a complete food, in particular substances containing lipids, proteins or carbohydrates, and at least one active principle, and in which, notably:

- the active principle remains stable for a long period,
- the presence of the active principle in the composition does not affect the animals' appetite for this composition,
- the formulation selected allows effective masking of the taste of the active principle when this active principle has an unpleasant taste,
- the active principle is distributed homogeneously in the composition, both in each dosage unit and from one dosage unit to another,
- the active principle is released in appropriate quality and quantity for obtaining the preventive or curative pharmaceutical effect required, notably owing to the fact that it is included in a nutritional composition that has a long residence time in the stomach,
- the specific characteristics of the composition do not require the use of a complex and/or expensive method of preparation; said composition can be prepared using an industrial manufacturing chain of a known type
- the method employed does not have an adverse effect on the stability of the active principle and its content.

After considerable research, the applicant developed a method for preparing nutritional and medicinal oral compositions that is simple to implement and that makes it possible to manufacture compositions having the advantageous properties specified above.

The present invention relates to a method for obtaining a nutritional and medicinal oral composition for veterinary use comprising the following steps:

a) supplying cores of complete feed extrudate, and
b) coating the cores of complete feed extrudate supplied in step a) with at least one layer of fat comprising at least one medicinal agent, said medicinal agent comprising (i) at least one preconditioned active principle in the form of a solution or of a suspension of said active principle in an oily liquid or (ii) at least one preconditioned active principle in the form of waxy granules, at a temperature below 40° C.

The extrudate cores that are supplied in step a) include (i) the extrudate cores comprising a mixture of nutritional substances that have not undergone a final treatment step by surface application of fat or liquefied oil at a high temperature, i.e. in a "hot" process, said cores are also called "crude extrudate cores", and (ii) the extrudate cores prepared according to a method comprising a step of surface application of fat or hot liquefied oil, said cores are also called "treated extrudate cores", for the purposes of the present description.

Surprisingly, the applicant has shown that the "cold" incorporation of a medicinal agent as defined in the present description in a fat or oil composition forming a coating layer of a core of complete feed extrudate imparts great stability over time to the active principle that is contained in said medicinal agent, i.e. both (i) protection of the active principle against degradation by the external environment and (ii) protection of the active principle against degradation caused by contact of the latter with the substances contained in the extrudate core. It will be understood that this characteristic makes it possible to prevent, or at least substantially reduce, degradation of active principles that are sensitive to hydrolysis.

In particular, the fact that the medicinal agent is incorporated "cold" in the coating layer of fat or oil, without a step of liquefaction by heating, preserves the active principle contained in said medicinal agent against any effect of degradation by heat.

Moreover, the applicant has shown that "cold" incorporation of the medicinal agent in the coating layer of fat or oil prevents, or at the very least substantially reduces, penetration of the fat or oil contained in the coating layer into the bulk of the extrudate core. This specific characteristic prevents any degradation of some or all of the active principle contained in the medicinal agent owing to contact of the latter with the extrudate core. This characteristic also makes it possible, owing to the presence of all or almost all of the medicinal agent in the coating layer, to control the profile of release of the active principle, with the aim of obtaining an optimal pharmacological effect.

It is thus shown that the particular combination of characteristics of the oral veterinary composition above allows optimal release of the active principle(s) of interest, so as to induce an optimal preventive or therapeutic medicinal effect. In particular, it is shown that with an oral veterinary composition as defined above, administered as a food, a profile of release of the active principle is obtained which is of the slow or prolonged release type, which allows effective plasma concentrations of said active principle to be maintained for a longer time than with a medicinal product with immediate release and thus allows increased overall activity of said active principle on the target sites of the latter in the animal's body. This means that with an oral veterinary composition according to the invention, a given preventive or curative pharmaceutical effect can be obtained with a smaller amount of active principle(s) than with conventional compositions (AUC equivalent to and Cmax lower than the reference treatment).

It has also been shown according to the invention that the nutritional and medicinal oral composition that is obtained at the end of the above method has excellent properties of palatability for animals, even when the active principle is bitter or repellent for the animal.

It is particularly important that the feedstuff has excellent palatability. In fact, it is recognized that cats are very sensitive to the taste of their feed and this effect is more pronounced when a cat is ill. A side effect resulting from the disease, notably renal, in cats, is loss of appetite. It is therefore crucial to be able to treat a sick cat effectively before it refuses to eat altogether. Moreover, for daily treatment, it is very important to ensure very good palatability; in fact it is necessary to avoid the animal associating the medicated feed with an unpleasant taste, which makes compliance disastrous within a few days.

"Core of complete feed extrudate" means, according to the invention, the central part of the oral composition that consists of a mixture of nutritional elements, notably lipids, proteins and carbohydrates, in quality and in quantity suitable for feeding the animals for which the oral composition is intended. In other words, an oral veterinary composition according to the invention contains the nutrient elements essential for the animals for which it is intended.

The central part or core is in the form of a product obtained by extrusion of a nutritional raw material or of a mixture of nutritional raw materials, for example a mixture (i) of raw materials derived from cereals, (ii) of raw materials derived from meat, egg or fish and (iii) of fats of animal or vegetable origin. The use of an extrudate is entirely conventional in the food industry, in particular for making feed pellets intended for animals, in particular for companion animals such as dogs and cats.

As already stated above, an extrudate core comprises a crude extrudate core and a treated extrudate core, the treated extrudate core having been obtained by a method comprising a step of application, generally by vapor deposition or spraying, at high temperature, of a fat or oil composition which has been liquefied beforehand by heating.

For the purposes of the present description, the term "active principle" denotes an active pharmaceutical ingredient accepted by a person skilled in the art, i.e. a substance that is included in the composition of a medicinal product and that endows said medicinal product with its preventive or curative therapeutic properties.

For the purposes of the present description, an active principle (i) preconditioned in the form of a solution or of a suspension of said active principle in an oily liquid or (ii) preconditioned in the form of waxy granules may also be called "medicinal agent" or "medicated premix". A medicinal agent according to the invention may comprise a single active principle or else a plurality of active principles, for example 2, 3 or 4 separate active principles.

In certain embodiments of a medicinal agent comprising a plurality of preconditioned active principles in an oily liquid, all the active principles may be dissolved in the oily liquid.

In other embodiments of a medicinal agent comprising a plurality of preconditioned active principles in an oily liquid, all the active principles may be suspended in the oily liquid.

In yet other embodiments of a medicinal agent comprising a plurality of preconditioned active principles in an oily liquid, at least one of the active principles is dissolved in the oily liquid and at least one other of the active principles is in suspension in said oily liquid.

Thus, in the present description, the term "medicinal agent" denotes the physical form in which the active principle is incorporated, i.e. either (i) in the form of a solution of said active principle in an oily liquid or in the form of an oily suspension of said active principle, or (ii) in the form of waxy granules, in which said active pharmaceutical ingredient is included in a powder of a hydrophobic wax.

According to the invention, an active principle may be preconditioned by incorporating said active principle in a hydrophobic wax, i.e. mainly by incorporating an active principle in the form of particles of active principle included in a hydrophobic wax at a temperature between 15° C. and 25° C., for example in the form of waxy granules. The preconditioned active principle in the form of waxy granules is advantageously in the form of a powder of particles of hydrophobic wax in which the active principle is distributed. Preferably, the preconditioned active principle in the form of waxy granules is in the form of a powder of particles of hydrophobic wax in which particles of the active principle are distributed.

Method of Obtaining an Oral Veterinary Nutritional and Medicinal Composition

In step a), as has already been stated above, the cores of complete feed extrudate are advantageously prepared by conventional techniques, for example techniques of preparation of raw materials, mixing thereof, then extrusion, especially extrusion/cooking, of the mixtures obtained, which are commonly used in the area of the manufacture of pellets for animals, in particular for companion animals, including dogs or cats.

In certain embodiments of the method, the extrudate cores consist of cores of "treated extrudate", which are prepared by a method comprising a step of treatment of a crude extrudate as described above by application of a fat or an oil liquefied beforehand by heating, as described for example in PCT application No. WO 2012/099786 or in patent application No. US 2010/0303968 and in PCT applications Nos. WO 2010/138372 and WO 2011/091111.

For preparing the extrudate cores, raw materials may be used that are easily accessible commercially.

In certain embodiments of the method, step b) comprises the following steps:
 b1) bringing the cores of complete feed extrudate into contact with at least one medicinal agent, said medicinal agent comprising (i) at least one preconditioned active principle in the form of a solution or of a suspension of said active principle in an oily liquid or (ii) at least one preconditioned active principle in the form of waxy granules, and
 b2) coating the extrudate cores obtained at the end of step b1) with at least one layer of fat, at a temperature below 40° C.

In these embodiments of the method, the extrudate cores are brought into contact with the medicinal agent prior to the step of coating with the layer of fat. In these embodiments, the medicinal agent subsequently penetrates into the coating layer of fat, within which, notably, the active principle is protected from degradation through contact with the external environment.

Step b1) may be carried out by mixing the medicinal agent with the extrudate cores, prior to the step of coating with the layer of fat. Preferably, step b1) is carried out at a temperature below 40° C.

In other embodiments of the method, step b) comprises the following steps:
 b3) obtaining a fat composition comprising at least one medicinal agent, said medicinal agent comprising (i) at least one preconditioned active principle in the form of a solution or of a suspension of said active principle in an oily liquid or (ii) at least one preconditioned active principle in the form of waxy granules, and
 b4) coating the extrudate cores obtained at the end of step a) with at least one layer of the fat composition comprising said medicinal agent, obtained at the end of step b3), at a temperature below 40° C.

In step b4), the extrudate cores are preferably coated by kneading or mixing the cores of extrudate, crude extrudate or treated extrudate, with a layer of fat comprising the medicinal agent that comprises the active principle(s) of interest. Preferably, a medicinal agent is used that comprises an active pharmaceutical ingredient that is either (i) in the form of a solution or of an oily suspension of the active principle(s), or (ii) in the form of preconditioning of the active principle(s) in a hydrophobic medium, preferably a wax, i.e. in the form of waxy granules.

Regardless of the embodiment of the method that is employed, step b), notably step b) comprising steps b1) and b2 or step b) comprising steps b3) and b4), is preferably carried out at a temperature below 40° C., better still below 35° C., preferably below 30° C., and especially preferably below 25° C. At these temperatures of carrying out step b), no degradation of the active principle(s) or of the other constituents of the oral veterinary composition is observed. Notably, degradation of the proteins contained in the core of complete feed extrudate and degradation of the vitamins are avoided, and oxidation of the fats is also avoided.

According to a preferred embodiment, the whole of the method according to the invention is carried out at a temperature as stated above, namely below 40° C.

In general, the fat composition used for coating step b) comprises at least one fat of animal or vegetable origin.

As has already been stated and as will be described in more detail later on in the present description, the active principle may be preconditioned in liquid form; either the active principle is dissolved in the liquid, or the active principle is suspended in the liquid.

In other embodiments of the medicinal agent, the active principle is in the form of particles and is preconditioned by incorporation in a hydrophobic wax, i.e. in the form of waxy granules.

The active principle(s) constituting the medicinal agent used in step b) of the method is(are) defined elsewhere in the present description.

The Coating Fat Composition

Various lipid substance(s) may be contained in a coating layer of fat of the oral veterinary composition, in particular including lipid substances of natural origin, in particular fats of animal or vegetable origin.

According to certain variants of the method, the layer of fat comprises at least one fat selected from hog fat, lard, suet, duck fat or fish oil.

Notably, the fat may be of various origins. The fat may be selected from beef tallow, poultry fat, soybean oil, canola oil, sunflower oil, fish oil, lard, or white fat.

The lipid substances may notably be selected from:
(i) the following lipid substances of natural origin: beeswax, lanolin, hog fat, lard, suet or fish fat, fish oil, carnauba wax, soybean oil, peanut oil, colza oil, paraffin, microcrystalline wax, petroleum jelly, and a mineral oil, and
(ii) the following lipid substances of synthetic origin: fatty alcohol, fatty acid, ester of alcohol and fatty acid (white wax), polyethoxylated vegetable oil, hydrogenated vegetable oil, mono-, di- and triglycerides of fatty acids.

In a preferred variant of the invention, the lipid substance of natural origin is a mineral oil. In another preferred variant of the invention, the lipid substance of synthetic origin is an alcohol or a fatty acid or a mixture thereof.

Advantageously, most of the lipid substances contained in the coating layer of fat of an oral veterinary composition according to the invention have a melting point above 30° C., preferably above 40° C., and are therefore in solid form at the usual storage temperatures of food products or pharmaceuticals.

Preferably, the coating layer of fat is in the form of a paste that can easily be worked at a temperature well below its melting point. The fat paste is preferably obtained by kneading, or creaming, the lipid substance or the combination of lipid substances constituting the coating fat.

In certain embodiments, the core of complete feed extrudate is coated with a plurality of layers of fat, with at least one coating layer of fat comprising at least one medicinal agent.

In general, the number of coating layers of fat varies from 1 to 5. Most often, an oral veterinary composition according to the invention comprises a single coating layer of fat, which comprises at least one active pharmaceutical ingredient.

In these embodiments, the coating layer of fat comprising the medicinal agent(s) consists of the outer layer of the composition, said outer layer being in contact with the external environment.

In the above embodiments, the coating layer of fat comprising at least one medicinal agent may consist of animal fat, for example poultry fat, typically duck fat or goose fat, or else lard.

Medicinal Agent

In certain embodiments of an oral veterinary composition according to the invention, the active principle(s) of interest comprised in the medicinal agent is(are) in dissolved form in an oily solution, or else in the form of a suspension in an oily liquid, notably depending on the solubility characteristics of said active principle(s).

Oily solution or oily liquid means a hydrophobic solution comprising an oil or a mixture of oils. An oil may be of natural or synthetic origin, in particular an animal, vegetable or mineral oil.

In the embodiments in which the active principle is suspended in an oily liquid, said oily liquid may comprise, besides the oily vehicle itself, also one or more substances selected from viscosity adjusters, resuspending agents, antioxidants, preservatives, pigments, flavorings and perfumes.

The viscosity adjusters may be selected from silica, aluminum mono-, di- and tristearate and hydrogenated castor oil.

The resuspending agents may be selected from the amphiphilic surfactants, which include the fatty acids or the lecithins.

The antioxidants may be selected from BHA, BHT, propyl gallate or else vitamin E, or a mixture of these excipients.

In certain advantageous embodiments of a medicinal agent according to the invention, the active principle is in the form of particles.

In these embodiments, the active principle of the medicinal agent may be an oily suspension of the particles of active principle or else the medicinal agent may be in the form of waxy granules, in which the particles of active principle are distributed.

In these embodiments, the active principle(s) of interest in the form of particles is(are) preferably in the form of microparticles.

Advantageously, the average size of the microparticles of active principle is less than 400 µm, or 100 µm, and better still less than 80 µm. The average size of the particles of active principle varies advantageously from 10 µm to 50 µm, and is preferably in the range from 15 µm to 35 µm. To measure the average particle size of active principle for the purposes of the present description, preferably the laser diffraction technique is used ("Low Angle Laser Light Scattering" or LALLS) according to the European Pharmacopeia and notably according to Ph. Eur. 2.9.31: Analysis of particle size by diffraction of laser light (standard ISO 13320: 2009 & 9276.1), according to Ph. Eur. 2.9.35 Fineness of powders, but also according to the method of analytical sieving (Ph. Eur. 2.9.38; ISO 3310.1), classification according to Ph. Eur. 2.9.12.

It is to be noted that the particles of active pharmaceutical ingredient quite preferably contain only said active principle, to the exclusion of any other compound. These non-encapsulated particles of active principle therefore do not have a layer of a material preventing contact of the active principle(s) with the external environment, and in particular do not have a protective layer intended to preserve the active principle against destructive effects of the external environment. The particles of active principle in particular do not have a layer for masking the odor or taste of the active principle.

It is shown, surprisingly, that the particulate, preferably micro-particulate, character of the active principle, combined with absence of a protective outer layer of the particles or microparticles (non-encapsulation), allows good adhesion and good maintenance of the active principle in the hydrophobic layer that is not in contact with the core of complete feed extrudate.

The inventors showed that specific advantages are obtained when the particulate active principle is included in said coating layer of fat in the form of a medicinal agent, i.e. after preconditioning in a lipid substance, and more specifically when the active principle is preconditioned in dissolved form in an oily liquid or in the form of an oily suspension or in the form of waxy granules.

The use of the active principle in the form of preconditioning in the form of a medicinal agent as defined in the present description (i) allows great stability of the active principle in the oral veterinary composition and (ii) endows the oral veterinary composition with properties of palatability leading to better compliance of ingestion of the oral veterinary composition by the animals. Moreover, in practical terms, it is easier for the operator to incorporate the medicinal agent in the extrudate cores, compared with incorporation of one or more active principles that are not preconditioned in the form of a medicinal agent.

Thus, in certain embodiments of an oral veterinary composition according to the invention, the medicinal agent comprises the particulate active principle(s) that is (are) preconditioned in the form of an oily suspension.

Moreover, in certain other embodiments of an oral veterinary composition according to the invention, the medicinal agent comprises the active principle(s) that is (are) preconditioned in the form of waxy granules, in which the particles of active principle(s) are incorporated.

Active Principles

Owing to the fact that the oral veterinary compositions of the invention comprise both (i) at least one medicinal agent and (ii) nutrients in appropriate quality and quantity for complete nutrition of the animals, said oral veterinary compositions are suitable for use for preventing or treating diseases, in particular for treating chronic diseases, which requires daily administration of active principle(s) over a long period of time, for example for several months or several years, or even throughout the animal's life.

The chronic diseases that can be prevented or treated with an oral veterinary composition according to the invention include hepatic, renal, vascular, digestive, inflammatory, infectious or respiratory-tract chronic diseases.

An oral veterinary composition according to the invention is specifically advantageous when prevention or treatment of a disease requires both (i) administration of one or more active pharmaceutical ingredient(s) and (ii) application of a suitable diet.

An oral veterinary composition as defined in the present description may notably be used for treating renal insufficiency.

The active principles that may be used in a medicinal agent constituting an oral veterinary composition of the invention include metronidazole, neomycin, bronchodilators such as aminophylline, nonsteroidal anti-inflammatory drugs such as carprofen, meloxicam, robenacoxib, mavacoxib, firocoxib, deracoxib, ciclosporin, S-adenosyl-methionine, beta-blockers, aldosterone receptor inhibitors, such as eplerenone or spironolactone, amlodipine, pimobendan, levosimendan, torasemide, furosemide, alkaloids such as theophylline, antiangiogenic agents, etc.

In the case of renal insufficiency in particular, said active principle may be selected from the angiotensin-converting enzyme inhibitors (ACE inhibitors), renin inhibitors and angiotensin II receptor antagonists (compounds ending in "-sartan" such as losartan), the angiotensin-converting enzyme inhibitors (ACE inhibitors), renin inhibitors and angiotensin II receptor antagonists.

The angiotensin-converting enzyme inhibitors that may be used in an oral veterinary composition of the invention include benazepril, enalapril, ramipril, quinapril, preindopril, lisinopril, imidapril, zofnopril, trandolapril, as well as salts thereof.

The renin inhibitors that may be used in an oral veterinary composition of the invention include pepstatin, the peptide analogs of pepstatin such as H-142, the peptide mimetics of pepstatin such as remikiren and the non-peptide mimetics of pepstatin such as aliskiren, as well as salts thereof.

The angiotensin II receptor antagonists that may be used in an oral veterinary composition of the invention include valsartan, telmisartan, losartan, irbesartan, azilsartan and omesartan, as well as salts thereof.

The active principles that may be used in a medicinal agent constituting an oral veterinary composition of the invention also include firocoxib, ciclosporin, S-adenosylmethionine, eplerenone, spironolactone, amlodipine and levosimendan. As stated above, an oral veterinary composition according to the invention may comprise, as active pharmaceutical ingredient, benazepril or a salt thereof. An oral veterinary composition of this kind is useful in the prevention or treatment of renal insufficiency.

According to certain embodiments, an oral veterinary composition of the invention useful for animals that are affected, or likely to be affected, by renal insufficiency comprises (i) benazepril and (ii) a core of complete feed extrudate whose qualitative and quantitative constitution of nutrients is suitable for maintaining renal function in the case of chronic renal insufficiency, for example a core of complete feed extrudate having a low phosphorus content as well as a low content of proteins, said proteins being of high quality.

Advantageously, benazepril is used in the form of benazepril hydrochloride.

Advantageously, benazepril or a salt thereof is present in an amount varying from 0.0025 to 0.0100% (25 to 100 ppm) by weight, relative to the total weight of the oral veterinary composition. For example, an oral veterinary composition according to the invention may comprise about 50 ppm by weight of benazepril or of a salt thereof, relative to the total weight of said oral veterinary composition.

Core of Complete Feed Extrudate

The term "extrudate" is used in the present description in its conventional sense known by a person skilled in the art. The complete feed extrudate is the end product of a method comprising a step during which a suitable mixture of nutrients is passed through the die of an extruder.

In general, a person skilled in the art can easily determine the appropriate qualitative and quantitative constitution of nutrients of the core of complete feed extrudate contained in an oral veterinary composition according to the invention, based on his general knowledge in the area of the preparation of feedstuffs for animals, including in the area of feedstuffs for companion animals such as dogs and cats, which includes feedstuffs in the form of pellets.

In general, said extrudate core comprises nutrients in appropriate quality and quantity, for example in quality and quantity defined according to the regulatory standards, including the standards of the government health authorities, such as the Direction Générale de l'Alimentation (General Food Directorate) attached to the French Ministry of Agriculture, the European Food Safety Authority (EFSA), the Center for Veterinarian Medicine attached to the Food and Drug Administration of the United States, or the "American Feed Control Officials Incorporated" of the United States.

The constituents used for preparing the extrudate core of an oral veterinary composition according to the invention include, but are not limited to, farinaceous substances, proteinaceous substances, and fats, in the form of mixtures. In certain embodiments, the extrudate core may comprise proteins, substances containing starch, substances containing fibers, fats, mineral substances, vitamins, in the form of mixtures or combinations of at least two of these constituents.

The protein substances include meat, and meat derivatives, chicken, lamb or mutton, turkey, beef, goat meat and fish. Meat derivatives include lungs, kidneys, livers, stomachs and intestines.

Substances containing starch include substances derived from cereals, especially substances derived from maize, wheat, rice, oats, or sorghum.

Substances containing fibers include fructooligosaccharides, beet pulp, the mannan-oligosaccharides, oat fiber, pulp of citrus fruits, carboxymethylcellulose, as well as gums such as gum arabic, guar gum, or apple or tomato pomaces, and mixtures or combinations thereof.

Fats include fats of animal origin and fats of vegetable origin.

Fats of animal origin include those that are derived from chicken, turkey, pork, beef, or from fish, as well as mixtures or combinations thereof.

Fats of animal origin include fish oils. Fats of vegetable origin include vegetable oils such as maize oils, soybean oils, cotton oils, palm oils, coconut oils, as well as mixtures and combinations thereof.

Mineral substances include sodium selenite, monosodium phosphate, calcium carbonate, potassium chloride, ferrous sulfate, zinc oxide, manganese sulfate, copper sulfate, manganese oxide, potassium iodide, cobalt carbonate, as well as mixtures and combinations thereof.

The vitamins include choline chloride, vitamin E, ascorbic acid, vitamin A acetate, calcium pantothenate, pantothenic acid, biotin, thiamine monoitrate, vitamin B12, niacin, riboflavin, inositol, pyridoxine hydrochloride, vitamin D3, folic acid, vitamin C, as well as mixtures and combinations thereof.

The core of complete feed extrudate may also comprise amino acids such as methionine, leucine, lysine, tryptophan, arginine, cysteine, aspartic acid, taurine, as well as mixtures and combinations thereof.

The core of complete feed extrudate may comprise additional substances such as antioxidants, stabilizers, binders, thickeners, taste exhausters, flavorings, preservatives, fillers, emulsifiers, sweeteners, buffering agents, dyes, gelling agents and humectants.

The emulsifiers and/or gelling agents include gelatin, cellulose ethers, starch, starch esters, starch ethers and modified starches. Starch includes ungelatinized starch, fully gelatinized starch and partially gelatinized starch, and mixtures or combinations thereof. Partially or fully gelatinized starch may be in the form of pregelatinized starch, which is hydrated at the moment of use.

Notably, the core of complete feed extrudate may comprise additional substances such as carotenoids, polyphenols, fatty acids, probiotics, or prebiotics.

In certain embodiments of an oral veterinary composition according to the invention, the quality and quantity of nutritional substances are adapted to the specific physiology of the animals with renal insufficiency, especially cats with renal insufficiency.

In these embodiments, said extrudate core comprises lipids, carbohydrates and proteins and has a reduced phosphorus content and a reduced protein content, relative to the commonly accepted normal values.

In certain embodiments, known cores of complete feed extrudate may be used, whose qualitative and quantitative composition of ingredients is suitable for a diet intended for animals, especially cats, with chronic renal insufficiency. It is possible for example to use extrudate cores that are described in PCT application No. WO 2007/084986.

In these embodiments, said extrudate core may for example comprise (i) 5 to 50 wt % of proteins, (ii) from 0.001 to 1 wt % of sodium, and (iii) from 0.01 to 1 wt % of potassium, the percentages by weight being expressed relative to the total weight of said extrudate core. In these embodiments, said extrudate core may for example comprise (i) 8 to 25 wt % of proteins, (ii) from 0.05 to 0.6 wt % of sodium, and (iii) from 0.05 to 0.9 wt % of potassium, the percentages by weight being expressed relative to the total weight of said extrudate core. In these embodiments, said extrudate core may for example comprise (i) 10 to 16 wt % of proteins, (ii) from 0.1 to 0.5 wt % of sodium, and (iii) from 0.1 to 0.5 wt % of potassium, the percentages by weight being expressed relative to the total weight of said extrudate core. In these embodiments, said extrudate core may for example comprise (i) 5 to 30 wt % of proteins, (ii) from 0.01 to 2 wt % of sodium, (iii) from 0.01 to 2 wt % of potassium, and (iv) from 0.2 to 1 wt % of phosphorus, the percentages by weight being expressed relative to the total weight of said extrudate core. In these embodiments, said extrudate core may for example comprise (i) 25 to 50 wt % of proteins, (ii) from 0.1 to 2 wt % of sodium, (iii) from 0.1 to 2 wt % of potassium, and (iv) from 0.2 to 1 wt % of phosphorus, the percentages by weight being expressed relative to the total weight of said extrudate core.

In one variant, the invention is more specifically suitable for treating or preventing renal insufficiency. In this case, the core of complete feed extrudate comprises an amount of starch of at most 25 wt %, for example an amount of starch in the range from 20 to 25 wt %, for example an amount of starch in the range from 10 to 15 wt %, relative to the total weight of said extrudate core. Advantageously, the core of complete feed extrudate comprises phosphorus and sodium in suitable amounts.

Advantageously, said extrudate core comprises essentially, or comprises exclusively, proteins of animal origin.

Advantageously, said extrudate core also comprises vitamins, and in particular one or more of the following vitamins: vitamin A, vitamin D, vitamin E, vitamin K, vitamin B1, vitamin B2, vitamin B3, vitamin B6, biotin, folic acid and vitamin B12.

Advantageously, said extrudate core comprises one or more trace element(s). In particular, said extrudate core may comprise one or more additional elements selected from copper, iron, iodine, manganese, magnesium, selenium and zinc.

Other Characteristics of the Oral Veterinary Composition

Advantageously, the extrudate core of an oral veterinary composition according to the invention represents from 75 to 95 wt %, relative to the total weight of said composition.

Advantageously, the total of the layers of fat coating said extrudate core represents from 5 to 25 wt %, relative to the total weight of said composition, it being understood that the weight of the medicinal agent(s) contained in at least one of the layers of fat is negligible relative to the total weight of the oral veterinary composition.

The coating layer of fat comprising the medicinal agent(s) must be present in a sufficient amount for protecting the active principle(s) contained in said medicinal agent(s) against contact with the external environment, and in particular against contact with water that may be present in the external environment, including in the form of water present in a humid atmosphere.

In certain embodiments of the oral veterinary composition of the invention, the coating layer of fat comprising the active principle(s) represents from 4 to 15 wt %, relative to the total weight of said composition. In these embodiments, the oral veterinary composition comprises a plurality of layers of fat, the layer(s) of fat other than the coating layer comprising the medicinal agent advantageously representing from 1 to 10 wt %, relative to the total weight of said oral veterinary composition.

In advantageous embodiments, an oral veterinary composition according to the invention, the coating layer of fat containing the active principle(s) represents from 0.5 to 15 wt %, the percentages by weight being expressed relative to the total weight of said oral veterinary composition. In these embodiments, the oral veterinary composition comprises a plurality of layers of fat, the layer(s) of fat other than the coating layer comprising the medicinal agent advantageously representing from 4 to 10 wt %, relative to the total weight of said oral veterinary composition.

In the embodiments of the oral veterinary composition of the invention in which the medicinal agent comprises at least one active principle in the form of an oily suspension of the latter, at least a proportion, if not all, of the oil contained in the oily suspension of initial active principle is present in the coating layer of fat comprising said active principle. In these specific embodiments, the layer of fat comprising the active principle may comprise from 0.05 to 2 wt % of the oil derived from the oily suspension of active principle, relative to the total weight of said oral veterinary composition.

Without wishing to be bound by any theory, the applicant thinks that, in the above embodiments, the particles of active principle are, within the coating layer of fat which comprises them, covered partially or completely with a film of oil derived from the initial oily suspension. Said film of oil is of a nature to further reinforce the protection of the active principle against possible harmful effects caused by the external environment. Moreover, the presence of said oil film on the surface of the particles of active principle may contribute to the characteristics of the pharmacokinetic profile of the oral veterinary composition. Finally, the presence of said oil film on the surface of the particles of active principle could also produce an effect of masking the taste or odor of the active principle with respect to the olfactory or gustatory sensitivity of the animals and thus reinforce the properties of palatability of the oral veterinary composition of the invention.

Moreover, in a composition according to the invention, the active principle is included in a nutritional composition so that said composition has a long residence time in the stomach. With a composition according to the invention, gastric emptying is substantially delayed in comparison with the gastric emptying observed on ingestion of a pharmaceutical formulation, including a delayed-release pharmaceutical formulation. In consequence, inclusion of the active principle in the mass of a composition comprising a core of complete feed extrudate contributes substantially to obtaining a pharmacokinetic profile that is particularly suitable for the active principles whose target sites are located in the small intestine, such as the angiotensin-converting enzyme inhibitors such as benazepril. As an illustration, it is known that the gastric residence time of a dry food, for example pellets, in the gastric cavity of a cat is about 14 hours to 16 hours. By definition, an identical gastric residence time is expected with a nutritional and medicinal oral composition according to the invention that allows release of the whole of the active principle contained initially in this composition in the stomach before gastric emptying occurs, and thus ensure optimal bioavailability of the active principle for the target sites. These characteristics of a nutritional and medicinal composition according to the invention are quite particularly advantageous for the active principles whose pharmacological effect is substantially increased on saturation of the target sites by these active principles.

In the embodiments of the oral veterinary composition of the invention in which the active principle is incorporated in the form of waxy granules, the layer of fat comprising the active principle may comprise from 0.05 to 2 wt % of the wax, relative to the total weight of said oral veterinary composition.

Advantageously, the weight ratio of the coating layer of fat to the medicinal agent will be between 1/5 and 1/10, preferably about 1/7.

In these embodiments, the applicant thinks that the layer of wax coating the particles of active principle has the functions described above for the oil film.

Premix or Preconditioning Composition in the Form of an Oily Suspension of Active Principle As is disclosed in the present description, a preferred first starting form of an active principle, or preferred premix composition, used for making an oral veterinary composition according to the invention, is an oily suspension of said active principle. This is a particular embodiment of a medicinal agent according to the invention.

For the oily suspension, an oil is used whose melting point is below 10° C., which includes the oils whose melting point is below 9° C., 8° C., 7° C., 6° C., 5° C., 4° C., 3° C., 2° C., 1° C. or 0° C. In general, an oil is used whose melting point is above −10° C.

The oil constituting the oily suspension may comprise, or consist of, a triglyceride or a mixture of triglycerides, or a polyol ester.

It is possible for example to use a triglyceride of capric acid and/or of caprylic acid, which is notably marketed under the name Miglyol® 810 or Miglyol® 812 by the company Sasol (Germany).

It is also possible to use triglycerides of capric acid/capric acid/linoleic acid, which are notably marketed under the name Miglyol® 818 by the company Sasol (Germany).

It is also possible to use triglycerides of caprylic acid/capric acid/succinic acid, which are notably marketed under the name Miglyol® 829 by the company Sasol (Germany).

It is also possible to use an oil of the propylene glycol dicaprylate/dicaprate type, which is notably marketed under the name Miglyol® 840 by the company Sasol (Germany).

The oily suspension comprises at least one active principle, advantageously at a rate from 0.1 to 10 wt %, for example from 0.5 to 5 wt %, for example about 1 wt %, relative to the total weight of said oily suspension.

The oily suspension of active principle may also comprise one or more fillers intended to control the density of said suspension so as to allow homogeneous distribution of the particles of active principle throughout the volume of the suspension, and so as to avoid, or at the very least greatly reduce, sedimentation of the particles of the active principle. The viscosity adjuster, when it is present in the oily suspension, advantageously represents from 0.5 to 3 wt %, better still from 1 to 2 wt %, and even better about 1.0 wt %, relative to the total weight of said oily suspension. As an illustration, the viscosity adjuster may be colloidal silica, for example Aerosil® 200 (Evonik Industries).

The oily suspension of active principle may also comprise at least one surfactant, which can improve resuspension. The surfactant, when it is present in the oily suspension, advantageously represents from 0.1 to 3.0 wt %, better still from 1 to 2 wt %, and even better about 1.5 wt %, relative to the total weight of said oily suspension. For example, a nonionic surfactant may be used, such as Tween® 80 (Sigma Chemical).

Thus, the present invention also relates to a premix composition, in particular for making a nutritional and medicinal composition for veterinary use, comprising an oily suspension of particles of active principle, for example an oily suspension of benazepril, which is not microencapsulated.

Premix or Preconditioning Composition in the Form of Hydrophobic Medium, Notably a Wax, in which the Active Principle is Incorporated As is disclosed in the present description, a preferred second initial form of an active principle, or preferred premix composition, used for making an oral veterinary composition according to the invention, consists of a hydrophobic wax in which particles of active principle are incorporated. This is another particular embodiment of a medicinal agent according to the invention.

A hydrophobic medium of this kind is preferably obtained by techniques of waxy granulation, which are familiar to a person skilled in the art.

Waxy granulation of the particles of active principle may be carried out in an air-fluidized bed, by kneading or by mixing.

The step of waxy granulation may be carried out by spraying a solution comprising at least one waxy compound and a solvent.

In certain embodiments, the solution comprising the waxy compound and the solvent may also include at least one viscosity adjuster.

The coating solvents are those used conventionally by a person skilled in the art. We may mention as examples water, methylene chloride, ethanol, isopropanol and mixtures thereof.

This process is carried out in an air-fluidized bed, by kneading, by mixing or by any other similar industrial process known by a person skilled in the art.

The drying operation may be carried out in an air-fluidized bed, in a rotary dryer under vacuum or by any equivalent technique for removing the residual solvents.

The waxy compounds used may notably be selected from the group consisting of: waxes, Novata waxes, Gélucires (Gattefossé) and Suppocires (Gattefossé), glyceric macrogols, fatty acids (of the stearic acid type), esters of fatty acids, glycerol monostearate, Précirols (Gattefossé), Compritols (Gattefossé).

Among these waxy compounds, advantageously the hydrophobic waxy compounds will be used, and even more advantageously hydrophobic waxy compounds having a low HLB (hydrophilic-lipophilic balance) and having a melting point between 35 and 53° C., preferably between 37 and 43° C. We may mention, nonexhaustively, the waxy compounds marketed under the names Gélucires 43/01 and NovataAB.

These waxy compounds may be combined with glycerol monostearate (GMS).

Hydrophobic waxy compounds may be used that have a low HLB (hydrophilic-lipophilic balance) and have a melting point between 35° C. and 53° C., preferably between 37° C. and 43° C. in the presence of lubricants. We may mention, nonexhaustively, Gélucire 43/01 and NovataAB, optionally combined with glycerol monostearate (GMS).

The waxy compound may also be glycerol palmitostearate, for example Precirol® AT05 (Gattefossé).

The starting solution also advantageously comprises a filler, such as a sugar, or a sugar derivative such as mannitol or xylitol.

In the paste end product, the active principle advantageously represents from 0.1 to 10 wt %, better still from 0.5 to 5 wt %, for example about 1 wt %, relative to the total weight of the wax composition containing the latter.

Advantageously, the waxy compound(s) are present in an amount ranging from 10 to 50 wt %, better still from 15 to 40 wt %, for example from 20 to 30 wt %, which comprises about 25 wt %, relative to the total weight of the wax composition containing the latter.

In the wax composition, the filler(s) may be present in a significant amount, for example at a rate of more than 50 wt %, even up to at least 75 wt %, relative to the total weight of said wax composition. The filler or fillers, when present, represent less than 80 wt %, relative to the total weight of the wax composition containing the latter.

Thus, the present invention also relates to a premix composition, in particular for making a nutritional and medicinal composition for veterinary use, comprising an oily suspension of particles of non-microencapsulated benazepril.

The present invention also relates to an oral composition as defined in the present description, for use as a medicinal product for veterinary use.

The invention also relates to an oral composition as defined in the present description, for use for preventing or treating a disorder or a disease in an animal, in particular in a companion animal, and especially a dog or a cat.

The invention notably relates to a composition as defined in the present description for use for preventing or treating renal insufficiency in a nonhuman mammal.

The invention also relates to the use of a composition as defined in the present description, for making a nutraceutical for preventing or treating renal insufficiency in a nonhuman mammal.

The present invention also relates to a method for preventing or treating a disorder or a disease in an animal, comprising a step in which a suitable amount of an oral veterinary composition as defined in the present description is administered to said animal, preferably by the oral route.

The present invention is further illustrated by the examples given below.

EXAMPLES

Example 1: Preparation of an Oral Veterinary Composition with a Preconditioned Active Principle in the Form of an Oily Suspension 1.1. Preparation of the Medicated Premix in the Form of Oily Suspension:

The active principle is benazepril hydrochloride in the form of a powder having an average particle size from 10 to 35 μm marketed by the company Aurobindo (India).

An oily suspension based on Miglyol®840 (Condea GmbH, Germany) is prepared, to which Aerosil®200 (colloidal silica—2% w/w) and Tween®80 (ester of polyethylene and sorbitol—0.5% w/w) are added.

The powder of active principle is added to the above oily suspension and the oily suspension is obtained by homogenizing by stirring using a stirrer of the Rotor Stator type until a homogeneous suspension is obtained. The final concentration of the active principle in the oily suspension was 1.0 wt %, relative to the total weight of the oily suspension.

1.2. Preparation of the Oral Veterinary Composition

A single-component complete feed extrudate of the RenalCat® type marketed by the company Virbac Nutrition is supplied in the form of pellets that have been treated by hot spraying of liquid fat (treated extrudate core).

The treated extrudate cores are coated by kneading in a paddle mixer of the kneader type, in the following operating conditions: introduction of the treated extrudate cores, introduction of the medicated premix prepared as described in § 1.1. above, and introduction of a mass of hydrophobic material, preferably duck fat, lard or fish oil, in a weight ratio of medicated premix/hydrophobic material of 1/7, mixing for max. 300 seconds.

In each pellet of the final composition, the hydrophobic layer containing the active principle represents about 12 wt %, relative to the total weight of the pellet.

Example 2: Preparation of an Oral Veterinary Composition with a Preconditioned Active Principle by Incorporation in a Wax 2.1. Preparation of the Preconditioned Active Principle in the Form of Waxy Granules The active principle is benazepril hydrochloride in the form of a powder having an average particle size from 15 to 30 μm marketed by the company Aurobindo (India).

Waxy granules of the active principle are prepared by dry granulation with a mixture of Precirol® ATO 5 (glycerol distearate) and Pearlitol® 160C (mannitol), at a rate of 1% (weight/weight) of benazepril hydrochloride, 25% (weight/weight) of Precirol® and 74% (weight/weight) of Pearlitol® in a granulator of the Rotolab type with double-jacket heating equipped with tools for mixing (impeller) and for breaking up lumps (chopper), in the following operating conditions: temperature setting 50 to 80° C., product temperature 50 to 70° C., stirring speed between 100 and 1000 rpm.

2.2. Preparation of the Oral Veterinary Composition

A complete feed extrudate of the Renal Cat® type marketed by the company Virbac Nutrition is supplied in the form of pellets that have been treated by hot spraying of liquid fat (treated extrudate core).

The pellets of treated extrudate are coated by kneading in a paddle mixer of the kneader type, in the following operating conditions: introduction of the treated extrudate cores, introduction of the medicated premix prepared as described in § 2.1. above, and introduction of a mass of hydrophobic material, preferably duck fat, lard or fish oil, in a weight ratio medicated premix/hydrophobic material of 1/7, mixing for max. 300 seconds.

The extrudates and the duck fat are introduced, mixed for 20 seconds and then the medicated premix is introduced (and other components such as vitamins), mixing for 90 seconds.

In each pellet of the final composition, the hydrophobic layer containing the active principle represents between about 4.77 wt % (first variant above) and 9.59 wt % (second variant above), relative to the total weight of the pellet.

Example 3: Stability of the Oral Veterinary Composition

In this example, the properties of stability of the oral veterinary compositions as described in examples 1 and 2 were evaluated.

A. Materials and Methods

Pellets of each of the oral veterinary compositions described in example 1 or in example 2 are stored in sealed three-ply bags (PE, OPP, AL).

The bags containing the pellets are placed in several chambers with controlled temperature and level of relative humidity (RH).

The storage conditions were as follows: (i) 5° C.; (ii) 25° C., 60% RH; (iii) 30° C., 65% RH and (iv) 40° C., 75% RH.

The stability of the active principle contained in the pellets was evaluated after different storage times in the conditions stated above. The stability of the active principle was evaluated by measurement by HPLC (high-performance liquid chromatography).

Operating Conditions

Medicated Premix (Medicinal Agent)

Column: Uptishère ODB (Length (cm): 25, ID (mm): 4.60, Grafting: C18, Granulometry (μm): 5, T° C. column furnace: 25° C., Flow: 0.8 ml/min, Injection: 20 μl, UV detection: 240 nm, Mobile phase: $KH_2PO_4$ 5 g/L (30%): Methanol (70%) Solvent for dilution: $MeOH/H_2O$ (70/30).

Preparation of the Solutions

Analysis solution of the premix according to example 1: The product is extracted with isooctane/$MeOH/H_2O$ mixture and microfiltered, the dilution is adjusted and then the product is injected into the column.

Analysis solution of the premix according to example 2: The product is extracted in ethanol, made up with water and microfiltered, the dilution is adjusted and then the product is injected into the column.

Medicated Feed:

Column: Uptishère ODB (Length (cm): 25, ID (mm): 4.60, Grafting: C18, Granulometry (μm): 5, T° C. column furnace: 25° C., Flow: 0.8 ml/min, Injection: 40 μl, UV detection: 240 nm, Mobile phase: $KH_2PO_4$ 5 g/L (30%): Methanol (70%) Solvent for dilution: $MeOH/H_2O$ (70/30).

The product is extracted with pure methanol, the dilution is adjusted and then the product is injected into the column.

TABLE 1

| Stability of the medicated premix suspension I | | | | |
|---|---|---|---|---|
| | 1.5 months | 3 months | 6 months | 12 months |
| 5° C. | 99.6 | 100 | 99.8 | 98.8 |
| 25° C./60% RH | 99.0 | 99.9 | 98.4 | 97.0 |
| 30° C./65% RH | 98.5 | 99.0 | 98.3 | 96.8 |
| 40° C./75% RH | 100 | 99.4 | 99.2 | — |

TABLE 2

Stability of the medicated feed made from I

|  | 1.5 months | 3 months | 6 months | 9 months | 12 months |
|---|---|---|---|---|---|
| 5° C. | 102.3 | 98.3 | 95.9 | 98.4 | 102 |
| 25° C./60% RH | — | — | 100.1 | 93.2 | — |
| 30° C./65% RH | — | — | 93.3 | 87.8 | 90.6 |
| 40° C./75% RH | 86.0 | 92.4 | 74.7 | — | — |

TABLE 3

Stability of the medicated premix waxy granules II

|  | 1.5 months | 3 months | 6 months |
|---|---|---|---|
| 25° C./60% RH | 100.7 | 100. | 98.9 |
| 40° C./75% RH | 97.9 | 97.5 | 92.7 |

TABLE 4

Stability of the medicated feed made from II

|  | 1.5 months | 3 months | 6 months | 9 months | 12 months | 18 months | 24 months |
|---|---|---|---|---|---|---|---|
| 25° C./60% RH | 99.5 | 92.2 | 99.2 | 92.4 | 96.7 | 95.1 | 85.8 |
| 40° C./75% RH | 87.6 | 78.9 | 72.1 | — | — | — | — |

B. Results

The results obtained showed that:

for the medicated premix according to example 1, the content of active principle is 99.2% after storage for 6 months at 40° C. and 75% relative humidity and is 96.8% after storage for 12 months at 30° C. and 65% relative humidity;

for the medicated premix according to example 2, the content of active principle is 98.9% after storage for 6 months at 30° C. and 65% relative humidity and is 92.7% after storage for 6 months at 40° C. and 75% relative humidity;

for the oral veterinary composition according to example 1, the content of active principle is 98.4% after storage for 9 months at 4° C. and is 93.2% after storage for 9 months at 25° C. and 60% relative humidity;

for the oral veterinary composition according to example 2, the content of active principle is 94.9% after storage for 18 months at 25° C. and 60% relative humidity.

The results show that the specific characteristics of an oral veterinary composition of the invention allow a high level of stability in storage, although the particles of active principle are not coated with a protective layer against moisture, and are not micro-encapsulated, which runs counter to what a person skilled in the art expects, who believes that encapsulation is indispensable for preservation of the active principle.

Example 4: Palatability Properties of the Oral Veterinary Composition

In this example, the palatability properties of oral veterinary compositions obtained according to the details in examples 1 and 2 were evaluated.
A. Materials and Methods
A.1. Test system
A.1.1 Characterization The characteristics of the cats are given below.
Breed: European
Number: 21
Sex: 10 female and 11 male
Age: average 2.9 years; min.: 1.5 months-max.: 5.8 years
Weight: 3.88 kg; min.: 2.28 kg-max.: 5.45 kg
Identification: An identification card was placed on the doors of the boxes housing the animals showing the code of the study, the identifying number, breed, sex and date of birth of the cat.

The animals were in good health at the time of inclusion and had not received treatment in the 15 days preceding the start of the study.

A.1.2 Conditions for housing and maintenance

The animals remained in their usual housing locations. Maintenance was carried out every day except Sunday. The environmental parameters were recorded every day. A photoperiod of 12 h of light and 12 h of darkness was maintained. Food was distributed every day except Sunday. Being a criterion of the study, the distribution and withdrawal of food are presented in the paragraph "A.3.2 Administration conditions". Water was available ad libitum.

A.1.3 Constitution of the Groups and Acclimatization

During the test week, the animals were fed individually in the morning until about 16 h. So that they should become accustomed to these housing conditions, they were placed in individual cages in the same conditions in the first study week.

A.2. Treatments

The products were distributed randomly. On the first test day, each cat is placed in a kennel in the morning between 7 h and 9 h. The food, 80 g of test product, was offered to the animal. The behavior of the cat was observed and was reported on the observation cards. The food bowls were removed between 12 h and 14 h and the amounts of pellets that remained were weighed.

Test Products:
A: reference food, Renal Cat®
B: medicated feed with waxy granules
C: medicated feed with suspension, batch 1
D: medicated feed with suspension, batch 2
A.3. Test procedure
A.3.1 Experimental plan The study took place over 4 weeks. On the first day, each cat is placed in an individual cage between 7 h and 9 h. The food, 80 g of test product, was offered to the animal. The behavior of the cat was observed and reported on the observation cards. The food bowls were removed between 14 h 30 and 16 h 30 and the amounts of pellets that remained were weighed.

A.3.2. Administration conditions

In the first week, all the animals were fed with Renal Cat® food (marketed by the company Virbac Nutrition).

Then, for the subsequent weeks, on Monday the animals were all fed with the reference food, in the morning.

On Tuesday to Friday, the cats received 4 consecutive days of randomized administration of each of the test products, including the reference food.

From the first to the last test day, the person distributing the pellets applied the following scheme:
Distribution:
1: Weigh 80 g of pellets in a pot, note the exact amount in the "animal feeding" notebook.
2: Distribute the food bowl with the pellets to the cat
3: Observe the animal during distribution and complete the observation card Withdrawal:

Between 14 h30 and 15 h30, weigh the food bowl (food bowls+remaining pellets) and record this in the "animal feeding" notebook A.3.3 Clinical signs Clinical observation was carried out during distribution and withdrawal of the food bowls. If an animal required treatment not envisaged in the context of this study, the study director (veterinarian) agreed with the orderer on the treatment to be undertaken. However, if a prolonged delay would have caused the animal unacceptable suffering, the study director could administer the appropriate treatment, the orderer being informed of this as soon as possible. None of the animals in the study required any treatment beyond those envisaged.

B. Results

B.1 Food Consumption

The first week of administration of Renal Cat® is regarded as the week of acclimatization of the animals to the food and to the housing conditions. The results obtained during this week are not used for the rest of the calculations.

The average amounts ingested per food are presented in Table 5 below.

TABLE 5

| | Food | | | |
|---|---|---|---|---|
| | A | B | C | D |
| Amount (g) | 50 | 50 | 48 | 50 |

B.2. Conclusion

Twenty-one cats were fed for 4 weeks with an oral veterinary composition according to example 1 or example 2 or with the reference food Renal Cat®. The food was distributed in the morning and removed between 14 h30 and 15 h30. The animals were observed every day. For all the formulas tested, some clinical signs (vomiting) were recorded without the general condition of the animal being affected.

All the feedstuffs demonstrate good palatability, showing that incorporation of benazepril in the food did not alter the cats' food intake.

Example 5: Modeling of the Profile of Release of the Active Principle

The pharmacological efficacy of the active principle contained in an oral veterinary composition according to the invention was evaluated, then the results of this evaluation were compared with the level of pharmacological efficacy of a known pharmaceutical formulation containing the same active principle.

The active principle is benazeprilat, derived from the prodrug benazepril as contained in the oral veterinary compositions described in example 1.

The profile of the pharmacological effect of the compositions described in example 1 was compared with the profile of the pharmacological effect of a pharmaceutical formulation of tablets containing granules of benazepril coated with a polymer layer, marketed under the name Fortekor®.

A. Materials and Methods

Three experimental groups of six cats were prepared, respectively:
  Group 1: control animals fed with a composition similar to that described in example 1, but not containing benazepril;
  Group 2: the oral veterinary composition described in example 1 containing benazepril, and
  Group 3: the known reference composition Fortekor® The cats in Group 2 were fed with the oral veterinary composition described in example 1 and ingested a daily amount of benazeprilat of about 600 µg/kg.

The cats in Group 3 ingested tablets of Fortekor® at a rate of a daily dose of benazeprilat of 600 µg/kg. The cats were fed immediately after ingesting the tablets containing benazepril HCl.

The treatment of the cats in each of the three groups was carried out for eight consecutive days.

Blood samples were taken regularly from each cat in each of the three groups throughout the test. For each blood sample collected, the amount of benazeprilat was measured by tandem mode mass spectrometry (LC-MS/MS). For each blood sample collected, the activity of the angiotensin-converting enzyme (ACE) was measured. The percentage inhibition of ACE was calculated using the blood level of ACE activity of the cats in Group 1 as reference (0% inhibition).

A PK/PD analysis based on the physiological model described by Toutain et al. (2000) was performed for estimating the pharmacokinetics (PK) and pharmacodynamics (PD) of the two groups tested.

The profiles of the pharmacological effect (percentage inhibition of the angiotensin-converting enzyme (ACE) as a function of time) were determined for the various compositions using the model described by King et al. (2003, J Vet Pharmacol Ther, Vol. 26(3): 213-224), as described below.

B. Results

Figure 1A:
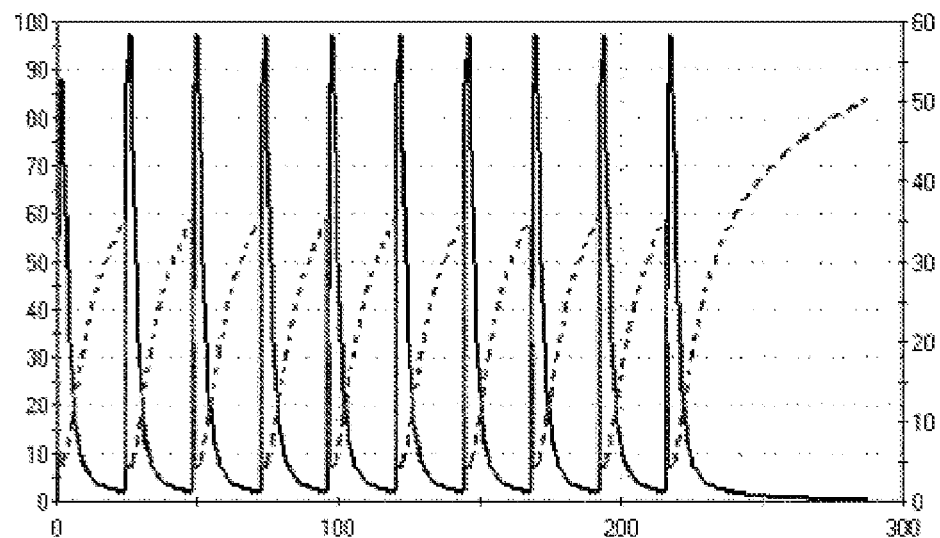
FIG. 1A: tablets of the pharmaceutical specialty Fortekor®.
Figure 1B:
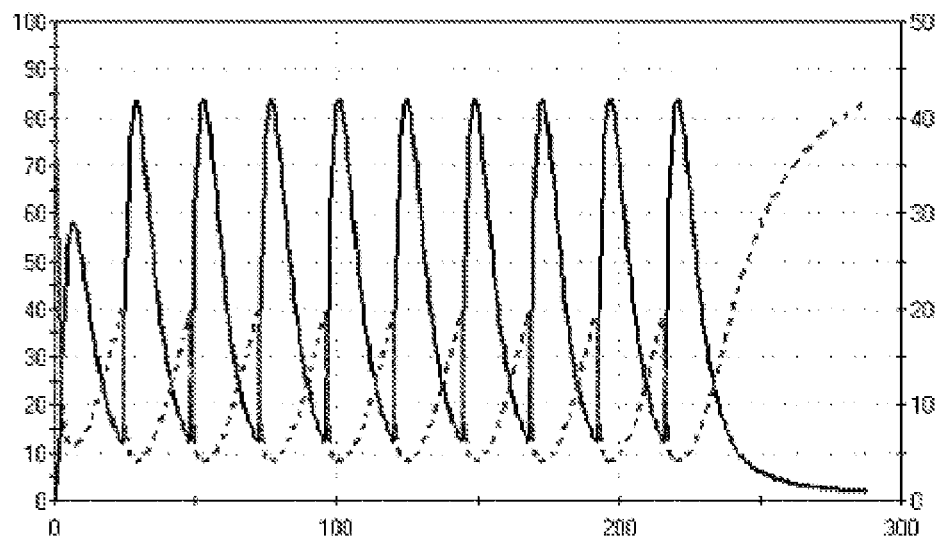
FIG. 1B: oral veterinary composition described in example 1

Predictive curves were obtained by modeling and are shown in FIGS. 1 and 2.

The results in FIG. 1 show that the pharmacokinetic profile and the pharmacological effect (% ACE inhibition) obtained with the oral veterinary composition are very different from those obtained with the composition Fortekor®. A "delay effect" can be seen for the Inv group (time difference in hours of the dotted curves relative to the Fortekor® group).

FIG. 2 illustrates comparison of the curves of ACE inhibition, respectively (i) with the oral veterinary composition described in example 1 "Inv" (continuous line) and (ii) with the Fortekor® composition (discontinuous line).

The results in FIG. 2 show that the composition Inv (overall average of 75.14% ACE inhibition) is substantially more effective than the Fortekor® reference composition (overall average of 59.62% ACE inhibition).

Example 6: Comparative Study of the Pharmacokinetic Profiles of a Composition According to the Invention (Inv) and of the Commercial Composition Fortekor®

A comparative study of the pharmacokinetic data (i) of an oral veterinary composition prepared as stated in example 1 ("Inv") and (ii) of the commercial composition Fortekor® was carried out.

The pharmacokinetic data were analyzed with the software Kinetica 5.0.

Summary of the Characteristics of the Study:

Reference: Fortekor 2.5 mg tablet (benazepril hydrochloride).

Test: Inv 50 mg benazepril hydrochloride/kg (of food), adm about 0.67 mg of hydrochloride benazepril/kg 12 cats, European male (3.7 to 4.5 kg, 3.1 to 6.4 years).

Oral administration for 8 days 2 groups in parallel (2×6 cats)

The food ration is fixed at 70 g of Renal Cat® alone or 50 g Inv+20 g Renal Cat®

Fortekor+(70 g) Renal Cat® (specific meal)

Inv (50 g)+(if everything was consumed) Renal Cat® (20 g)

Monitoring of food consumption (2 h after administration of the meal for Fortekor and 0.5, 2 and 6 h for Inv)

Collection of blood: T0 on D−1

D1 then at 2, 6, 8, 12 h after administration

D2, D3, D4, D5, D6, D7 and D8 before administration in the morning

D4 then at 2, 6, 8, 12 h after administration

D8 then at 2, 6, 8, 12 h, 24 h (D9) and 48 h (D10)

Method of analysis: LC/MS-MS, LOQ: 0.5 ng/mL for benazepril and benazeprilat

Monitoring of the Food Intake of the Cats in the Experiment Over 8 Successive Meals (D1 to D8) at 2 h (Fortekor Group) or 30 Min, 2 h, 6 h and 24 h (Inv Group) after Distribution of the Meal The results are presented in Table 6 below:

Food monitoring was carried out 30 min, 2 h, 6 h and 24 h after distribution of the meal for all the cats.

This table emphasizes the very good palatability of the product according to the invention.

VF very fast, F fast, S slow, VS very slow.

Table 6

Plasma Concentrations of Benazepril:

TABLE 7

| Time since treatment | Concentration of benazepril (ng/ml) | |
| --- | --- | --- |
| | Fortekor | Inv |
| Day 1 T0 | Nd | Nd |
| T2h | 8.48 ± 10.50 | 5.19 ± 2.55 |
| T6h | Nd | 4.27 ± 2.21 |
| T8h | Nd | 3.48 ± 2.29 |
| T12h | Nd | 3.02 ± 1.58 |
| Day 2 T0 | Nd | Nd |
| Day 3 T0 | Nd | Nd |
| Day 4 T0 | Nd | Nd |
| T2h | 8.08 ± 5.06 | 4.54 ± 2.28 |
| T6h | Nd | 5.35 ± 3.10 |
| T8h | Nd | 4.07 ± 3.00 |
| T12h | Nd | 3.37 ± 1.75 |
| Day 5 T0 | Nd | Nd |
| Day 6 T0 | Nd | Nd |
| Day 7 T0 | Nd | Nd |
| Day 8 T0 | Nd | Nd |
| T2h | 7.21 ± 2.56 | 5.21 ± 2.17 |
| T6h | 3.5 ± 3.43 | 4.79 ± 2.14 |
| T8h | 2.42 ± 2.75 | 3.55 ± 1.79 |
| T12h | 1.62 ± 1.77 | 3.1 ± 1.76 |
| T24h | Nd | Nd |
| T48h | Nd | Nd |

Lower benazepril concentrations are observed with Inv relative to Fortekor®, but they are maintained for 8 to 12 h.

Comparison of the PK/PD Parameters

TABLE 8

| PK parameters | D1 | D4 | D8 |
| --- | --- | --- | --- |
| | Cmax (ng/mL) | | |
| Fortekor | 7.67 ± 9.61 | 7.32 ± 4.89 | 7.21 ± 2.56 |
| Inv | 5.44 ± 2.27 | 5.80 ± 2.94 | 5.49 ± 2.16 |

TABLE 6

| Subject No. | Status | Food intake after 2 h for the 8 days | Status predominantly observed | Food intake on D1 | Food intake on D8 |
| --- | --- | --- | --- | --- | --- |
| 1 | Group 1 - Fortekor ® | 7 × all consumed in 2 h<br>1 × remainder 22 g after 2 h | VF and/or F | VF and/or F | S or VS |
| 2 | Group 1 - Fortekor ® | 6 × all consumed in 2 h<br>2 × remainder 3 & 15 g after 2 h | VF and/or F | S | S or VS |
| 3 | Group 1 - Fortekor ® | 8 × all consumed in 2 h | VF and/or F | VF or F | VF or F |
| 4 | Group 1 - Fortekor ® | 8 × all consumed in 2 h | VF and/or F | VF or F | VF or F |
| 5 | Group 1 - Fortekor ® | 5 × all consumed in 2 h<br>3 × remainder 15, 14 & 20 g after 2 h | * VF and/or F | S or VS | S or VS |
| 6 | Group 1 - Fortekor ® | 3 × all consumed in 2 h<br>5 × remainder 42, 40, 21, 18, & 17 g after 2 h | * Tendency to be S or VS | S or VS | VF or F |
| 7 | Group 2 - Inv | 8 × all consumed in 0.5 h | VF | VF | VF |
| 8 | Group 2 - Inv | 2 × all consumed in 0.5 h<br>6 × all consumed in 2 h | F and VF | VF | F |
| 9 | Group 2 - Inv | 8 × all consumed in 0.5 h | VF | VF | VF |
| 10 | Group 2 - Inv | 3 × all consumed in 6 h<br>5 × all consumed in 24 h | VS and S | VS | S |
| 11 | Group 2 - Inv | 8 × all consumed in 0.5 h | VF | VF | VF |
| 12 | Group 2 - Inv | 5 × all consumed in 2 h<br>3 × all consumed in 6 h | F and S | S | F |

TABLE 8-continued

| PK parameters | D1 | D4 | D8 |
|---|---|---|---|
| Tmax (h) | | | |
| Fortekor | 2.00 ± 0.02 | 2.02 ± 0.02 | 2.00 ± 0.00 |
| Inv | 3.34 ± 2.06 | 4.67 ± 2.06 | 4.00 ± 2.19 |
| AUClast (ng · h/mL) | | | |
| Fortekor | 8.72 ± 9.33 | 10.79 ± 13.09 | 39.98 ± 31.09 |
| Inv | 45.80 ± 20.41 | 48.21 ± 26.78 | 46.78 ± 19.66 |

Cmax is higher and more variable in group 1 (Fortekor®) than in group 2 (Inv) and Tmax is lower in group 1 (Fortekor) than in group 2 (Inv). Benazepril exposure is higher after administration of Inv.

Results for Plasma Concentration of Benazeprilat

Pharmacokinetic parameters of benazeprilat on D1, D4 and D8 for groups 1 (Fortekor®) and 2 (Inv):

TABLE 9

| PK parameter | day of analysis | | | Ratio of accumulation |
|---|---|---|---|---|
| | D1 | D4 | D8 | |
| Cmax (ng/mL) | Cmax 1 (n = 5) | | Cmax ss | =Cmax ss/Cmax 1 |
| Fortekor ® | 57.16 ± 22.69 | 43.64 ± 9.51 | 54.80 ± 27.03 | 1.02 ± 0.49 |
| Inv | 15.72 ± 3.78 | 20.08 ± 3.42 | 22.23 ± 2.82 | 1.47 ± 0.35 |
| Cmin (ng/mL) | Cmin 1 | | Cmin ss | =Cmin ss/Cmin 1 |
| Fortekor ® | 2.55 ± 1.31 | | 2.88 ± 0.92 | 1.20 ± 0.22 |
| Inv | 4.57 ± 1.49 | | 8.65 ± 3.25 | 2.02 ± 0.82 |
| Tmax (h) | | | | |
| Fortekor ® | 2.00 ± 0.02 | 2.02 ± 0.02 | 2.00 ± 0.00 | |
| Inv | 13.35 ± 5.49 | 9.66 ± 2.65 | 7.38 ± 3.29 | |
| AUClast (ng · h/mL) | | | | |
| Fortekor | 279.89 ± 107.70 | 270.23 ± 76.85 | 476.28 ± 172.44 | 1.44 |
| Inv | 242.11 ± 48.23 | 356.79 ± 46.93 | 504.48 ± 111.70 | 1.55 |

At steady state, Cmax was 2 times higher in the Fortekor® group relative to the Inv group.

TABLE 10

| Pharmacokinetic parameters (LC/MS-MS, LOQ 0.5 ng/mL) | | | |
|---|---|---|---|
| AUClast (ng · h/mL) | D1 | D4 | D8 |
| Fortekor ® | 279.89 ± 107.70 | 270.23 ± 76.85 | 476.28 ± 172.44 |
| Inv | 242.11 ± 48.23 | 356.79 ± 46.93 | 504.48 ± 111.70 |

The mean pharmacokinetic profiles of benazeprilat are shown in FIG. 6.

The kinetic profiles of the mean benazeprilat concentrations are different after administration of Fortekor® and after administration of Inv. The mean Cmax values for benazeprilat are lower, whatever day is considered, in the group treated with Inv relative to the group treated with Fortekor®.

The benazeprilat concentrations measured before each administration of the tablet, between D2 and D8, are higher after administration of Inv than after administration of Fortekor®. Better maintenance of the minimum benazeprilat concentrations is observed in group 2 (Inv) relative to group 1 (Fortekor®).

Results and Conclusions of the Test

The two products, Fortekor® and Inv, are in two different forms: a tablet and a medicated feed.

The average doses administered of the form of Fortekor and of Inv are approx. 600 µg/kg and approx. 510 µg/kg (mean values on D1). The dose administered in the form of Fortekor is therefore higher than the dose administered in the form of Inv.

Observations Concerning the Profiles

The results are illustrated notably in FIGS. 3, 4, 5 and 6.

There are two different formulations having two different profiles:

Administration of benazepril by the oral route (Fortekor®) in the form of a tablet produces a profile of the "adm bolus" type with a peak at 2 h (Tmax) reaching a maximum concentration (Cmax) fluctuating between 30 and 190 ng/mL followed by a decrease in the plasma concentrations (see FIG. 3). Therefore rapid and pronounced availability of benazeprilat is observed in the plasma but short persistence over time.

Administration of benazepril by the oral route (Inv) in the form of a medicated feed produces a profile of the "adm perfusion/delayed" type with an increase in the concentration over time, reaching a plateau (Tmax) between 6 and 12 h with a maximum concentration (Cmax) fluctuating between 10 and 71 ng/mL followed by a slow decrease in the plasma concentrations (see FIG. 4). Therefore slower and less pronounced availability of benazeprilat is observed in the plasma, with longer and constant persistence over time.

The forms of administration have a significant influence on the plasma profile of benazeprilat in the cat.

After observation of the pharmacokinetic data, and taking into account the dose actually administered, administration of benazepril in the form of medicated feed (Inv) always leads to an AUC last and to an AUC last corr of benazeprilat greater than those produced following administration of benazepril in the form of a tablet (Fortekor®), as is illustrated in FIGS. 4 and 5 respectively. We may therefore conclude from this that administration of the product according to the invention is at least as effective as the reference treatment, while offering a product that is very easy to administer and therefore allowing excellent compliance with the treatment. In addition, it should be pointed out that in this test, 100% of the cats took the Fortekor tablet, by gavage, provided by veterinarians accustomed to this procedure whereas in practice, in contrast, in the home of the cat's owner, effective ingestion of the tablet will be much more random, depending on the cat and the dexterity of the owner, making the results of product exposure even poorer for Fortekor than for the product according to the invention.

The invention claimed is:

1. A nutritional and medicinal oral composition for veterinary use comprising a core of complete feed extrudate coated with at least one layer of fat, said layer of fat comprising at least one medicinal agent, said medicinal agent comprising at least one preconditioned active principle in the form of non-encapsulated microparticles devoid of a protective outer layer, wherein the at least one preconditioned active principle is in the form of:
   (i) a solution or a suspension of said active principle in an oily liquid, or
   (ii) waxy granules.

2. The composition of claim 1, wherein the active principle is at least one selected from the group consisting of an angiotensin-converting enzyme inhibitor (ACE inhibitor), a renin inhibitor, an angiotensin II receptor antagonist, firocoxib, ciclosporin, S-adenosyl-methionine, eplerenone, spironolactone, amlodipine, and levosimendan.

3. The composition of claim 2, wherein the angiotensin-converting enzyme inhibitor is at least one selected from the group consisting of benazepril, enalapril, ramipril, quinapril, preindopril, lisinopril, imidapril, zofnopril, trandolapril, and salts thereof.

4. The composition of claim 2, wherein the renin inhibitor is at least one selected from the group consisting of pepstatin, a peptide analog of pepstatin, a peptide mimetic of pepstatin, and a non-peptide mimetic of pepstatin, and salts thereof.

5. The composition of claim 2, wherein the angiotensin II receptor antagonist is at least one selected from the group consisting of valsartan, telmisartan, losartan, irbesartan, azilsartan, omesartan, and salts thereof.

6. The composition of claim 1, wherein the active principle is benazepril or a salt thereof, in particulate form.

* * * * *